US012571057B2

(12) United States Patent
Kawata et al.

(10) Patent No.: US 12,571,057 B2
(45) Date of Patent: Mar. 10, 2026

(54) NUCLEIC ACID CONSTRUCT, KIT, DETECTION METHOD, AND THERAPEUTIC EFFECT PREDICTION METHOD

(71) Applicant: KABUSHIKI KAISHA TOSHIBA, Tokyo (JP)

(72) Inventors: Shigehisa Kawata, Niiza Saitama (JP); Mitsuko Ishihara, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 1119 days.

(21) Appl. No.: 17/552,652

(22) Filed: Dec. 16, 2021

(65) Prior Publication Data

US 2022/0220568 A1 Jul. 14, 2022

(30) Foreign Application Priority Data

Dec. 16, 2020 (JP) ................................ 2020-208491

(51) Int. Cl.

| | |
|---|---|
| ***C12Q 1/6897*** | (2018.01) |
| ***C07C 229/22*** | (2006.01) |
| ***C07C 229/24*** | (2006.01) |
| ***C07D 295/15*** | (2006.01) |
| ***C12Q 1/6886*** | (2018.01) |
| ***G01N 21/75*** | (2006.01) |
| ***G01N 33/50*** | (2006.01) |
| ***G01N 33/74*** | (2006.01) |

(52) U.S. Cl.

CPC .......... *C12Q 1/6897* (2013.01); *C07C 229/22* (2013.01); *C07C 229/24* (2013.01); *C07D 295/15* (2013.01); *C12Q 1/6886* (2013.01); *G01N 21/75* (2013.01); *G01N 33/5044* (2013.01); *G01N 33/743* (2013.01); *G01N 2333/723* (2013.01); *G01N 2800/52* (2013.01)

(58) Field of Classification Search

CPC ............................ C12Q 1/6897; C12Q 1/6886

See application file for complete search history.

(56) References Cited

U.S. PATENT DOCUMENTS

| | | | | | |
|---|---|---|---|---|---|
| 5,270,172 | A * | 12/1993 | Morgan | G01N 33/5011 436/501 |
| 2008/0003596 | A1 | 1/2008 | Akahoshi et al. | |
| 2014/0206037 | A1 * | 7/2014 | Slavcev | F16C 32/0629 435/367 |
| 2016/0303140 | A1 * | 10/2016 | Lee | A61P 35/00 |
| 2022/0220568 | A1 * | 7/2022 | Kawata | C07C 229/22 |
| 2023/0092732 | A1 * | 3/2023 | Kawata | G01N 33/5044 435/462 |

FOREIGN PATENT DOCUMENTS

| | | | |
|---|---|---|---|
| EP | 1 905 824 | A1 | 4/2008 |
| JP | 2007-202555 | | 8/2007 |
| JP | 2007-295806 | A | 11/2007 |
| JP | 2010-75064 | A | 4/2010 |
| JP | 5105864 | | 10/2012 |
| JP | 2022-89532 | A | 6/2022 |
| WO | WO 2006/129735 | A1 | 12/2006 |
| WO | WO 2021/079522 | | 4/2021 |
| WO | WO 2022/118918 | A1 | 6/2022 |

OTHER PUBLICATIONS

Japanese Office Action issued May 14, 2024 in Japanese Application 2020-208491, (with unedited computer-generated English translation), 10 pages.

Akahoshi et al., "Effect of dioxins on regulation of tyrosine hydroxylase gene expression by aryl hydrocarbon receptor: a neurotoxicology study", *Environmental Health*, vol. 8, No. 1, 2009, p. 24 (11 pages), DOI: 10.1186/1476-069X-8-24.

Hayashi, Shin-ichi et al., "Estrogen signaling pathway and its imaging in human breast cancer", *Cancer Science*, vol. 100, No. 10, 2009, pp. 1773-1778, DOI: 10.1111/j.1349-7006.2009.01243.x.

Matthews, et al., "Estrogen receptor and aryl hydrocarbon receptor signaling pathways", *Nuclear Receptor Signaling*, vol. 4, No. 1, 2006, p. nrs.04016 (4 pages), DOI: 10.1621/nrs.04016.

Gozgit, Joseph M. et al., "Differential action of polycyclic aromatic hydrocarbons on endogenous estrogen-responsive genes and on a transfected estrogen-responsive reporter in MCF-7 cells", Toxicology and Applied Pharmacology, vol. 196, No. 1, 2004, pp. 58-67.

Koizumi, Shinji et al., "A Versatile Transfection Assay System to Evaluate the Biological Effects of Diverse Industrial Chemicals", Biological and Pharmaceutical Bulletin, vol. 35, No. 10, 2012, pp. 1691-1696.

Poon, Ching Ho et al., "The citrus flavanone naringenin suppresses CYP1B1 transactivation through antagonising xenobiotic-responsive element binding", British Journal of Nutrition, vol. 109, No. 9, 2013, pp. 1598-1605.

Tarnow, Patrick et al., "A Novel Dual-Color Luciferase Reporter Assay for Simultaneous Detection of Estrogen and Aryl Hydrocarbon Receptor Activation", Chemical Research in Toxicology, vol. 30, No. 7, 2017, pp. 1436-1447.

* cited by examiner

*Primary Examiner* — Jonathan M Hurst

(74) *Attorney, Agent, or Firm* — Oblon, McClelland, Maier & Neustadt, L.L.P.

(57) ABSTRACT

According to one embodiment, a nucleic acid construct is used for detecting an estrogen-sensitive cell. The nucleic acid construct includes an enhancer sequence, a promoter sequence and a reporter gene. The enhancer sequence includes at least an ERE sequence and at least a XRE sequence. The promoter sequence is ligated to downstream of the enhancer sequence. The reporter gene is ligated to downstream of the promoter sequence.

23 Claims, 10 Drawing Sheets

Specification includes a Sequence Listing.

S1 — Introduction step of introducing nucleic acid construct into test cell

S2 — Addition step of adding estrogen to test cell

S3 — Culture step of culturing test cell

S4 — Detection step of detecting activity of reporter protein

S5 — Determination step of determining estrogen-sensitive cell from detection result

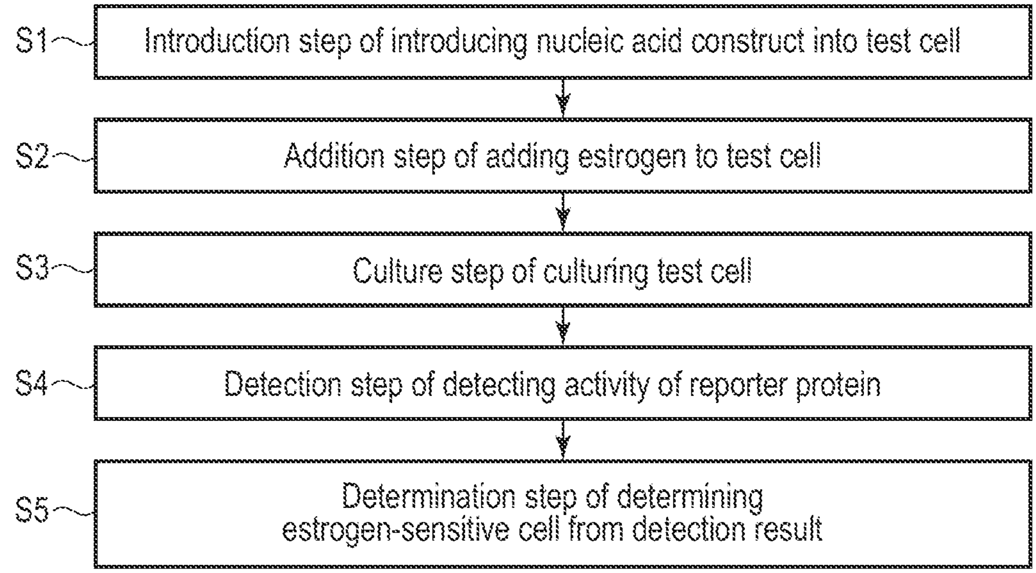

F I G. 4

S11 — Introduction step

S12 — Addition step

S13 — Culture step

S14 — Detection step

S15 — Prediction step of predicting efficacy of hormone treatment for subject

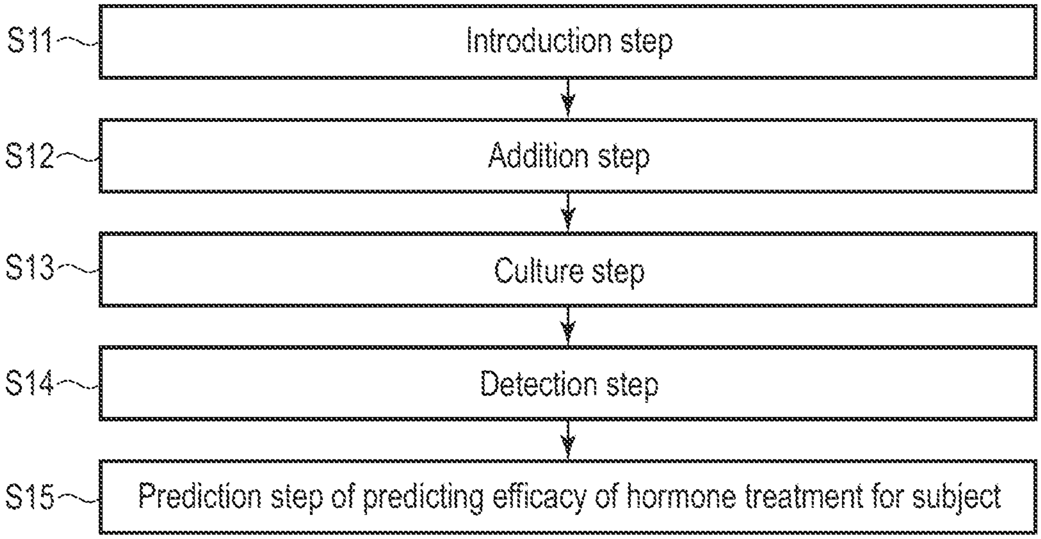

F I G. 5

Upstream pA 219..371
386 SacI (2)
ERE 451..462
ERE 482..494
ERE 524..535
ERE 557..569
ERE 598..609
ERE 631..643
minCMV 655..714
689 SacI (2)
743 XhoI (1)
NanoLuc 765..1314
BGHpA 1364..1591
SV40ori 2133..2457
ColE1 origin 3838..3156
AmpR 4595..3936
Vector (1)
ERE
4929bp
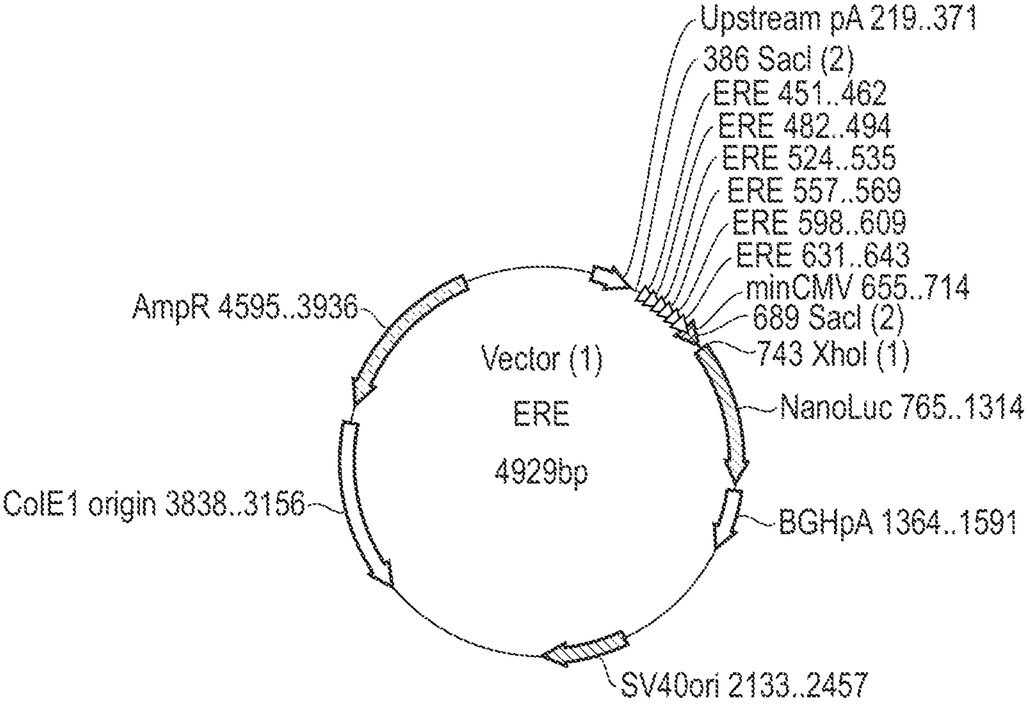
F I G. 8
Upstream pA 219..371
386 SacI (2)
AHRE-III 398..422
ERE 442..453
ERE 473..485
ERE 515..526
ERE 548..560
ERE 589..600
ERE 622..634
minCMV 646..705
680 SacI (2)
734 XhoI (1)
NanoLuc 756..1305
BGHpA 1355..1582
SV40ori 2124..2448
ColE1 origin 3829..3147
AmpR 4586..3927
Vector (2)
AhRE_ERE
4920bp
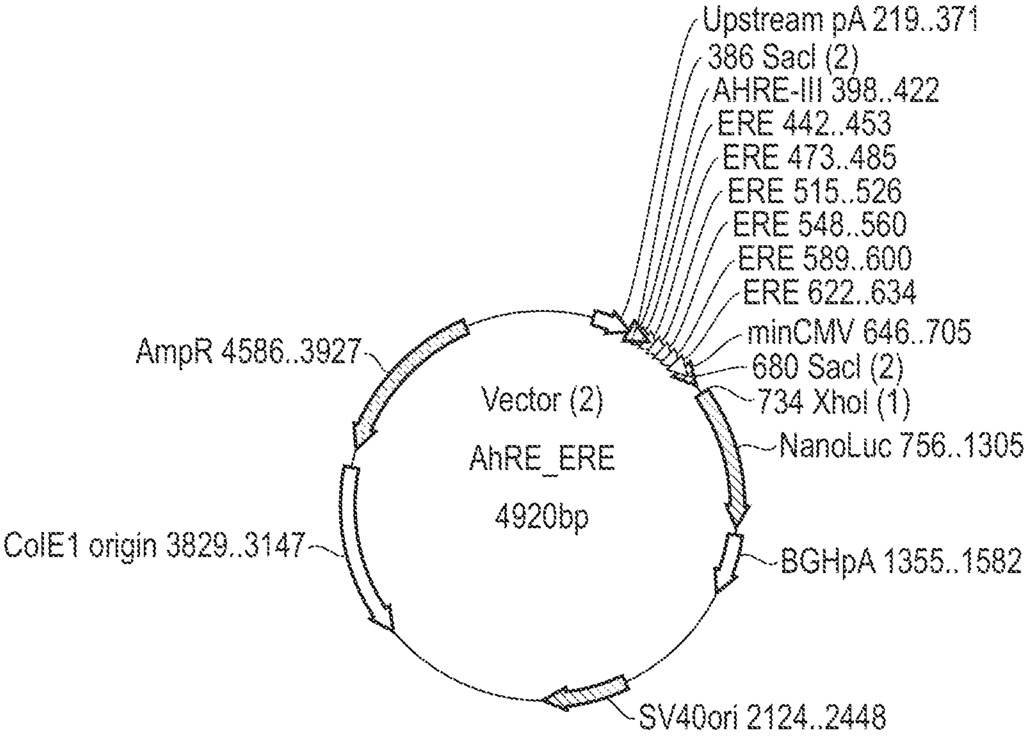
F I G. 9

SEQUENCE LISTING

```
<160> NUMBER OF SEQ ID NOS: 16

<210> SEQ ID NO 1
<211> LENGTH: 12
<212> TYPE: DNA
<213> ORGANISM: human

<400> SEQUENCE: 1

gaggtcatta tg                                                        12


<210> SEQ ID NO 2
<211> LENGTH: 13
<212> TYPE: DNA
<213> ORGANISM: human

<400> SEQUENCE: 2

atgcgcggtc aga                                                       13


<210> SEQ ID NO 3
<211> LENGTH: 12
<212> TYPE: DNA
<213> ORGANISM: human

<400> SEQUENCE: 3

ggtcatgatg ac                                                        12


<210> SEQ ID NO 4
<211> LENGTH: 13
<212> TYPE: DNA
<213> ORGANISM: human

<400> SEQUENCE: 4

gttggtcaga ttg                                                       13


<210> SEQ ID NO 5
<211> LENGTH: 12
<212> TYPE: DNA
<213> ORGANISM: human

<400> SEQUENCE: 5

catttcgacc ac                                                        12


<210> SEQ ID NO 6
<211> LENGTH: 13
<212> TYPE: DNA
<213> ORGANISM: human

<400> SEQUENCE: 6
```

-continued ggtcaggatg acc 13

<210> SEQ ID NO 7
<211> LENGTH: 213
<212> TYPE: DNA
<213> ORGANISM: human

<400> SEQUENCE: 7
ttctagacga gtttacttgg aggtcattat gaccacgatg tcgagtttac atgcgcggtc 60
agagtgacca cgtatgtcga gtttactccc acggtcatga tgaccacgta tgtcgagttt 120
acttggttgg tcagattgac cacgtatgtc gagtttataa ttcggtcatt tcgaccacgt 180
atgtcgagtt tactttcacg gtcaggatga cca 213

<210> SEQ ID NO 8
<211> LENGTH: 25
<212> TYPE: DNA
<213> ORGANISM: human

<400> SEQUENCE: 8
tgtcttcatg tcgtgtctag ggcgg 25

<210> SEQ ID NO 9
<211> LENGTH: 60
<212> TYPE: DNA
<213> ORGANISM: Cytomegalovirus

<400> SEQUENCE: 9
ggtaggcgtg tacggtggga ggcctatata agcagagctc gtttagtgaa ccgtcagatc 60

<210> SEQ ID NO 10
<211> LENGTH: 550
<212> TYPE: DNA
<213> ORGANISM: Oplophorus gracilirostris

<400> SEQUENCE: 10
agcttggcaa tccggtactg ttggtaaagc caccatggtc ttcacactcg aagatttcgt 60
tggggactgg cgacagacag ccggctacaa cctggaccaa gtccttgaac agggaggtgt 120
gtccagtttg tttcagaatc tcggggtgtc cgtaactccg atccaaagga ttgtcctgag 180
cggtgaaaat gggctgaaga tcgacatcca tgtcatcatc ccgtatgaag gtctgagcgg 240
cgaccaaatg ggccagatcg aaaaaatttt taaggtggtg taccctgtgg atgatcatca 300
ctttaaggtg atcctgcact atggcacact ggtaatcgac ggggttacgc cgaacatgat 360
cgactatttc ggacggccgt atgaaggcat cgccgtgttc gacggcaaaa agatcactgt 420
aacagggacc ctgtggaacg gcaacaaaat tatcgacgag cgcctgatca accccgacgg 480
ctccctgctg ttccgagtaa ccatcaacgg agtgaccggc tggcggctgt gcgaacgcat 540
tctggcgtaa 550

<210> SEQ ID NO 11
<211> LENGTH: 387
<212> TYPE: DNA
<213> ORGANISM: artificial
<220> FEATURE:
<223> OTHER INFORMATION: ERE-Promoter

<400> SEQUENCE: 11
tatcgatagg taccgagctc gctccgaatt cggctccgaa ttcgcccttc aggtccgagg 60

-continued

```
ttctagacga gtttacttgg aggtcattat gaccacgatg tcgagtttac atgcgcggtc    120

agagtgacca cgtatgtcga gtttactccc acggtcatga tgaccacgta tgtcgagttt    180

acttggttgg tcagattgac cacgtatgtc gagtttataa ttcggtcatt tcgaccacgt    240

atgtcgagtt tactttcacg gtcaggatga ccacgtatgt cgaggtaggc gtgtacggtg    300

ggaggcctat ataagcagag ctcgtttagt gaaccgtcag atcgcaaagg gcgaattcga    360

ccgaattcga cctcgagatc tgcgatc                                         387


<210> SEQ ID NO 12
<211> LENGTH: 20
<212> TYPE: DNA
<213> ORGANISM: artificial
<220> FEATURE:
<223> OTHER INFORMATION: Forward Primer

<400> SEQUENCE: 12

tatcgatagg taccgagctc                                                  20


<210> SEQ ID NO 13
<211> LENGTH: 16
<212> TYPE: DNA
<213> ORGANISM: artificial
<220> FEATURE:
<223> OTHER INFORMATION: Reverse Primer

<400> SEQUENCE: 13

gatcgcagat ctcgag                                                      16


<210> SEQ ID NO 14
<211> LENGTH: 75
<212> TYPE: DNA
<213> ORGANISM: artificial
<220> FEATURE:
<223> OTHER INFORMATION: Forward Primer

<400> SEQUENCE: 14

tatcgatagg taccgagctc gatatctgtc ttcatgtcgt gtctagggcg gttctagacg     60

agtttacttg gaggt                                                       75


<210> SEQ ID NO 15
<211> LENGTH: 138
<212> TYPE: DNA
<213> ORGANISM: artificial
<220> FEATURE:
<223> OTHER INFORMATION: Reverse Primer

<400> SEQUENCE: 15

gatcgcagat ctcgaggcga tctgacggtt cactaaacga gctctgctta tataggcctc     60

ccaccgtaca cgcctaccgt cgaattcggc cgccctagac acgacatgaa gacatcgaca    120

tacgtggtca tcctgacc                                                   138


<210> SEQ ID NO 16
<211> LENGTH: 69
<212> TYPE: DNA
<213> ORGANISM: artificial
<220> FEATURE:
<223> OTHER INFORMATION: Forward Primer
```

-continued

<400> SEQUENCE: 16
tatcgatagg taccgagctc tgtcttcatg tcgtgtctag ggcggacgta tgtcgaggta 60
ggcgtgtac 69

NUCLEIC ACID CONSTRUCT, KIT, DETECTION METHOD, AND THERAPEUTIC EFFECT PREDICTION METHOD

CROSS-REFERENCE TO RELATED APPLICATIONS

This application is based upon and claims the benefit of priority from Japanese Patent Application No. 2020-208491, filed Dec. 16, 2020, the entire contents of which are incorporated herein by reference.

FIELD

Embodiments described herein relate generally to a nucleic acid construct, a kit, a detection method, and a therapeutic effect prediction method.

BACKGROUND

Luminal type, a subtype of the breast cancer, is a breast cancer with estrogen receptor (ER) positive. The luminal type includes the cases where hormone therapy is effective and the cases where hormone therapy is not effective, and includes many cases in which hormone therapy is not effective. Therefore, accurate determination of which case is required for appropriate treatment.

Both cases differ in the mechanism of cancer progression. In the case where hormone therapy is effective, ER bound to the hormone as the ligand binds to an estrogen response element (ERE) sequence, whereby transcription of surrounding genes is promoted, and canceration proceeds. Whereas, in the case where hormone therapy is not effective, it is considered that although ER is expressed or overexpressed, transcription of genes around the ERE sequence is not promoted, and canceration proceeds by other mechanisms.

Therefore, there is a need for a method for detecting gene expression by binding of ER to an ERE sequence more accurately and with high sensitivity.

BRIEF DESCRIPTION OF THE DRAWINGS

FIG. 4 is a flowchart showing an example of a method for detecting estrogen-sensitive cells of the embodiment.

FIG. 5 is a flowchart showing an example of a therapeutic effect prediction method of the embodiment.

FIG. 8 is a view showing vector (1) produced in Example 1.

FIG. 9 is a view showing vector (2) produced in Example 1.

DETAILED DESCRIPTION

Figure 1:
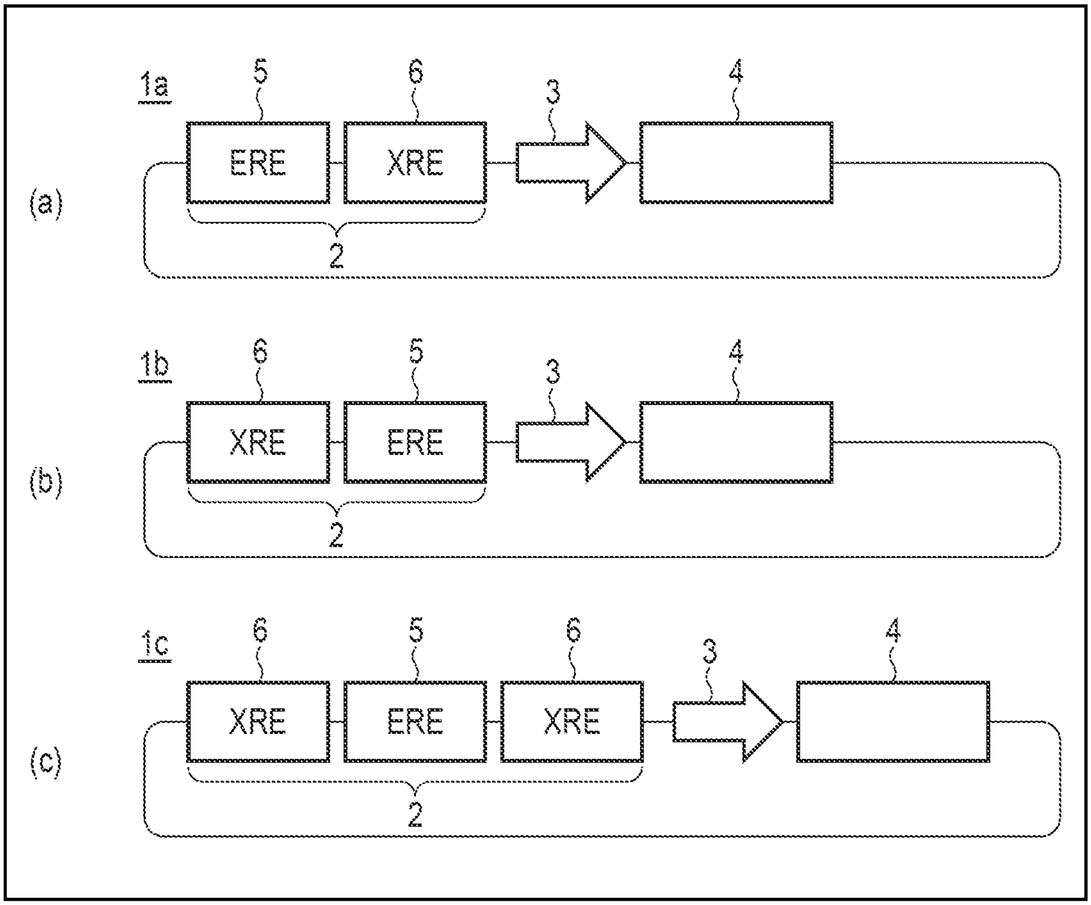
FIG. 1 is a diagram showing an example of nucleic acid construct of the embodiment.

In general, according to one embodiment, a nucleic acid construct is used for detecting an estrogen-sensitive cell. The nucleic acid construct includes an enhancer sequence, a promoter sequence and a reporter gene. The enhancer sequence includes at least an ERE sequence and at least a XRE sequence. The promoter sequence is ligated to downstream of the enhancer sequence. The reporter gene is ligated to downstream of the promoter sequence.

Various embodiments will be described hereinafter with reference to the accompanying drawings. The disclosure is merely an example, and proper changes in keeping with the spirit of the invention, which are easily conceivable by a person of ordinary skill in the art, come within the scope of the invention as a matter of course. In addition, in some cases, in order to make the description clearer, the widths, thicknesses, shapes and the like, of the respective parts are illustrated schematically in the drawings, rather than as an accurate representation of what is implemented.

However, such schematic illustration is merely exemplary, and in no way restricts the interpretation of the invention. In addition, in the specification and drawings, the same elements as those described in connection with preceding drawings are denoted by like reference numbers, and detailed description thereof is omitted unless necessary.

Nucleic Acid Construct

According to the embodiment, a nucleic acid construct is provided. The nucleic acid construct is, for example, linear or circular double-stranded DNA. The nucleic acid construct may be, for example, a vector. For example, the nucleic acid construct may be a vector based on a plasmid vector or a viral vector.

As illustrated in part (a) to (c) of FIG. 1, nucleic acid construct 1 (1*a*, 1*b*, and 1*c*) includes enhancer sequence 2, promoter sequence 3 ligated to downstream of enhancer sequence 2, and reporter gene 4 ligated to downstream of promoter sequence 3.

In the present description, "ligating" includes the case where ligating is performed between two sequences without including other sequences, and the case where an arbitrary sequence is included between two sequences. The arbitrary sequence is, for example, a spacer. The spacer is a nucleic acid sequence that is different from the sequences of the above sequences and the complementary sequences thereof and has less adverse effects on the activity of these sequences. The sequences are linked such that each function can be operated.

Enhancer sequence 2 includes at least an estrogen response element (ERE) sequence 5 and at least a xenobiotic responsive element (XRE) sequence 6.

In the nucleic acid construct, for example, as in nucleic acid construct 1*a* shown in part (a) of FIG. 1, enhancer sequence 2 includes ERE sequence 5 and XRE sequence 6 one by one in this order. Alternatively, for example, as in nucleic acid construct 1*b* shown in part (b) of FIG. 1, enhancer sequence 2 includes XRE sequence 6 and ERE sequence 5 one by one in this order. Alternatively, for example, as in nucleic acid construct 1*c* shown in part (c) of FIG. 1, enhancer sequence 2 includes ERE sequence 5 and two XRE sequences 6 ligated to upstream and downstream thereof. A spacer is preferably provided between the ligated ERE sequence 5 and XRE sequence 6.

The configuration of enhancer sequence 2 is not limited to the above one as long as enhancer sequence 2 includes ERE sequence 5 and XRE sequence 6 at least one by one. Hereinafter, the nucleic acid construct of the embodiment is also collectively referred to as nucleic acid construct 1.

Then, ERE sequence 5 and XRE sequence 6 will be described.

ERE sequence 5 includes, for example, at least one of base sequences of sequence numbers 1 to 6 shown in Table 1.

TABLE 1

ERE sequences

| Sequence number | Sequence |
|---|---|
| 1 | gaggtcattatg |
| 2 | atgcgcggtcaga |
| 3 | ggtcatgatgac |
| 4 | gttggtcagattg |
| 5 | catttcgaccac |
| 6 | ggtcaggatgacc |

ERE sequence 5 may be ligated by combining a plurality of any of the sequences in Table 1. In this case, a plurality of sequences different from each other may be included, or a plurality of sequences identical to each other may be included. For example, ERE sequence 5 is preferably a sequence in which 6 sequences shown in Table 1 are ligated in this order.

When a plurality of sequences are combined, a spacer is preferably arranged between the sequences. The base sequence of the spacer is not limited as long as it has a small adverse effect on the function of the sequence in Table 1. The base length of the spacer is preferably, for example, about 10 to 60 bases. For example, ERE sequence 5 may be a sequence of SEQ ID NO. 7 shown in Table 2.

TABLE 2

| ERE sequence (SEQ ID NO: 7) |
|---|
| ttctagacgagtttacttggaggtcattatgaccacgtgtcgagtttaca<br>tgcgcggtcagagtgaccacgtatgtcgagtttactcccacggtcatgat<br>gaccacgtatgtcgagtttacttggttggtcagattgaccacgtatgtcg<br>agtttataattcggtcatttcgaccacgtatgtcgagtttactttcacgg<br>tcaggatgacca |

The underlined portion represents the base sequence of SEQ ID NO. 1 to 6.

XRE sequence 6 is a sequence that is recognized and bound by allyl hydrocarbon receptor (AhR). XPE sequence 6 preferably includes, for example, at least one base sequence shown in Table 3. XRE sequence 6 may be a sequence in which a plurality of base sequences shown in Table 3 are ligated.

Table 3. XRE sequence (sequence ID number 8) tgtcttcatgtcgtgtctagggcgg

Alternatively, XRE sequence 6 may be a sequence including at least a core sequence GCGTG. In one embodiment, XRE sequence 6 is GCGTG.

Promoter sequence 3 is preferably selected from a virus-derived promoter or a tissue-specific promoter. The virus-derived promoter is, for example, a cytomegalovirus (CMV) promoter, a simian virus 40 (SV40) promoter, or a thymidine kinase (TK) promoter. The tissue-specific promoter is a promoter that is specifically used in the test cell derived tissue. Therefore, the tissue-specific promoter is selected according to the type of the test cell. For example, when the test cell is a breast cancer cell, it is preferable to use a mammary tissue-specific promoter, for example, an estrogen promoter or an estrogen receptor promoter. However, promoter sequence 3 is not limited to those listed above as long as it has the function of a promoter, and may be obtained by substituting or deleting any base in the base sequence of the above promoter sequence.

TABLE 4

| Promoter sequence of CMV (SEQ ID NO: 9) |
|---|
| ggtaggcgtgtacggtgggaggcctatataagcagacTctcgtttagtg<br>aaccgtcagatc |

Reporter gene 4 is, for example, a fluorescent protein gene, a luminescent protein gene, an active oxygen producing gene, or a drug resistance gene. For example, there can be used a fluorescent protein gene such as a blue fluorescent protein gene, a green fluorescent protein gene, or a red fluorescent protein gene; a luminescent enzyme protein gene such as a firefly luciferase gene, a renilla luciferase gene, or a NanoLuc® luciferase gene; a gene of active oxygen generating enzyme such as a xanthine oxidase gene or a nitrogen monoxide synthetase gene; a drug resistance gene such as a β-ampicillin resistance gene, a kanamycin resistance gene, a chloramphenicol resistance gene, a streptomycin resistance gene, a tetracycline resistance gene, a hygromycin resistance gene, a puromycin resistance gene, and a blasticidin resistance gene; or a heavy metal binding protein gene.

However, reporter gene 4 is not limited to the reporter genes listed above, and may be obtained by substituting or deleting any base of the base sequence of other reporter genes or the above reporter gene as long as it has a function as a reporter.

Reporter gene 4 is preferably, for example, a gene encoding NanoLuc® luciferase that is luciferase. An example of the base sequence is shown in Table 2.

TABLE 5

| Gene encoding Nanoluc ® (SEQ ID NO: 10) |
|---|
| AGCTTGGCAATCCGGTACTGTTGGTAAAGCCACCATGGTCTTCACACTC<br>GAAGATTTCGTTGGGGACTGGCGACAGACAGCCGGCTACAACCTGGACC<br>AAGTCCTTGAACAGGGAGGTGTGTCCAGTTTGTTTCAGAATCTCGGGGT<br>GTCCGTAACTCCGATCCAAAGGATTGTCCTGAGCGGTGAAAATGGGCTG<br>AAGATCGACATCCATGTCATCATCCCGTATGAAGGTCTGAGCGGCGACC<br>AAATGGGCCAGATCGAAAAAATTTTTAAGGTGGTGTACCCTGTGGATGA<br>TCATCACTTTAAGGTGATCCTGCACTATGGCACACTGGTAATCGACGGG<br>GTTACGCCGAACATGATCGACTATTTCGGACGGCCGTATGAAGGCATCG<br>CCGTGTTCGACGGCAAAAAGATCACTGTAACAGGGACCCTGTGGAACGG<br>CAACAAAATTATCGACGAGCGCCTGATCAACCCCGACGGCTCCCTGCTG<br>TTCCGAGTAACCATCAACGGAGTGACCGGCTGGCGGCTGTGCGAACGCA<br>TTCTGGCGTAA |

A transcription termination sequence may be further ligated to downstream of reporter gene 4. The transcription termination sequence is, for example, a poly (A) addition signal sequence of simian virus 40 (SV40), a poly (A) addition signal sequence of bovine growth hormone gene, or an artificially synthesized poly (A) addition signal sequence or the like. However, the transcription termination sequence is not limited thereto, and as long as it has a function as a transcription terminator, for example, another sequence or a modified base sequence of the above transcription termination sequence may be used.

Nucleic acid construct 1 may include any base sequence in addition to the above sequences. Such a base sequence may be, for example, a base sequence having a specific function or a sequence having no function. The base sequence having a function is, for example, an additional reporter gene expression unit, a replication initiation sequence, and/or a replication initiation protein expression unit.

According to nucleic acid construct 1 described above, cells sensitive to estrogen among the test cells can be visualized and discriminated. The principle will be described with reference to FIG. 2 and FIG. 3. Herein, an example using nucleic acid construct 1*a* in FIG. 1 will be described.

Figure 2:
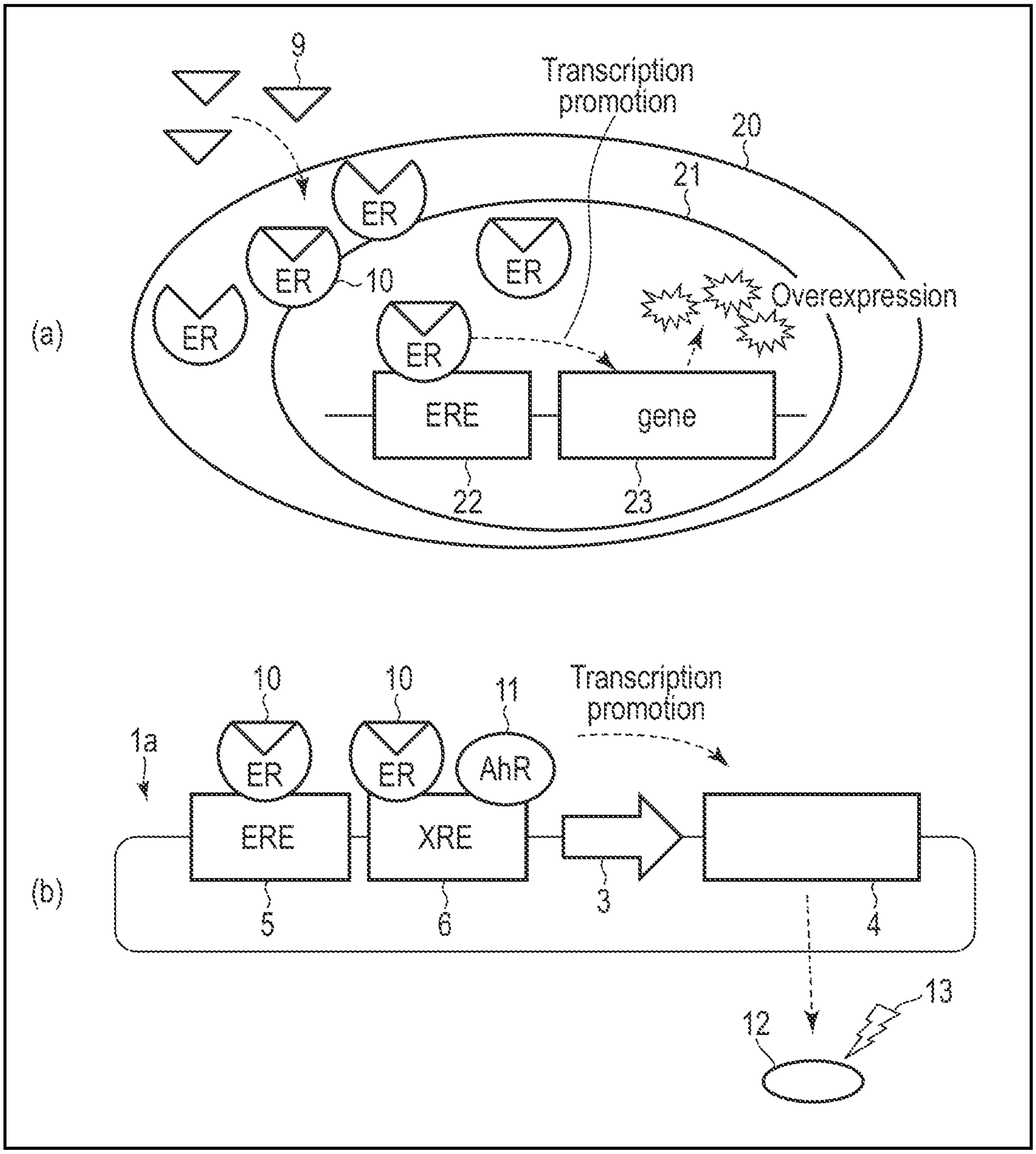
FIG. 2 is a diagram of estrogen-sensitive cells and an example of the behavior of the nucleic acid construct of the embodiment in estrogen-sensitive cells.

In test cell 20 shown in part (a) of FIG. 2, for example, an estrogen receptor (ER) is overexpressed, and the ER binds to ligand estrogen 9 supplied from outside of cell 20 to be formed into complex 10. Complex 10 moves into nucleus 21 and binds to ERE sequence 22 present on the genome. This binding causes overexpression of surrounding gene 23. Such test cell 20 is an estrogen-sensitive cell having the ability to promote transcription of surrounding genes by binding of ER to the ERE sequence. Test cell 20 may be, for example, a breast cancer cell in which hormone treatment is effective, among luminal breast cancers.

When nucleic acid construct 1*a* of the embodiment is introduced into test cell 20 and estrogen 9 is added, as shown in part (b) of FIG. 2, complex 10 binds to ERE sequence 5 and XRE sequence 6 of nucleic acid construct 1*a*. AhR11 may also bind to XRE sequence 6. As a result, the transcription of reporter gene 4 is promoted by ERE sequence 5 and XRE sequence 6, and reporter protein 12 can be generated. Reporter protein 12 exhibits detectable activity depending on the type, for example, producing signal 13.

Figure 3:
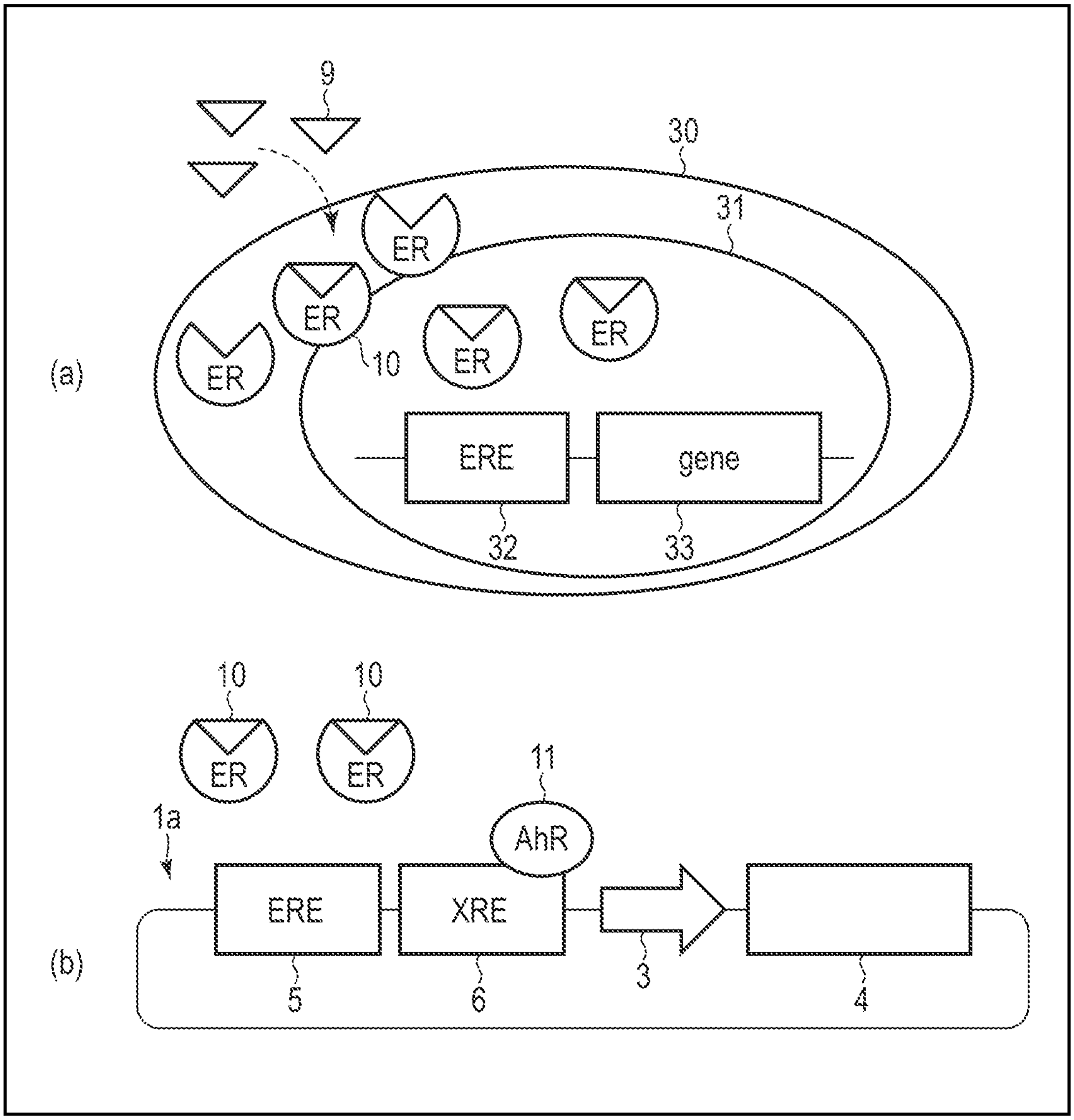
FIG. 3 is a diagram of estrogen-insensitive cells and an example of the behavior of the nucleic acid construct of the embodiment in estrogen-insensitive cells.

Whereas, in estrogen insensitive test cell 30 in which transcription promotion by binding of ER to ERE sequence shown in part (a) of FIG. 3 hardly occurs, when the ER is expressed or overexpressed, the ER does not bind to estrogen 9, or the ER bound to estrogen 9 (complex 10) does not bind to ERE sequence 32 in the cell. In a case where there is the binding, expression or overexpression of surrounding gene 33 does not occur. Test cell 30 may be, for example, a breast cancer cell in which hormone treatment is not effective, among luminal breast cancers.

When nucleic acid construct 1*a* of the embodiment is introduced into test cell 30 and estrogen 9 is added, as shown in part (b) of FIG. 3, formed complex 10 does not bind to ERE sequence 5 and XRE sequence 6, or complex 10 binding thereto does not promote transcription of reporter gene 4. Therefore, reporter protein 12 is not expressed or the expression level is low as compared with cell 20.

Therefore, a cell having high activity of reporter gene 4 of nucleic acid construct 1 can be determined to be an estrogen-sensitive cell. Conversely, a cell having a low activity of reporter gene 4 can be determined to be an estrogen insensitive cell.

As will be described in detail later, for example, it is also possible to calculate the abundance ratio of estrogen-sensitive cells detected as described above to determine the intensity of estrogen sensitivity as the total test cells. In addition, using the information, it is possible to predict whether or not hormone treatment is effective for cancer of a subject from which test cells are collected.

Method for Detecting Estrogen-Sensitive Cells

Hereinafter, a method for discriminating cells having sensitivity to estrogen from the test cells using nucleic acid construct 1 will be described. The method includes, for example, the following, as shown in FIG. 4. (S1) An introduction step of introducing a nucleic acid construct into a test cell; (S2) an addition step of adding estrogen to the test cell; (S3) a culture step of culturing the test cell; (S4) a detection step of detecting activity of a reporter protein expressed from a reporter gene; and (S5) a discrimination step of discriminating an estrogen-sensitive cell from the result of the detection step.

Hereinafter, the procedure of the method will be described in detail.

First, a test cell is prepared. The test cell is an animal cell, more preferably a mammalian cell, and most preferably a human cell. The test cell is, for example, a cell taken out of the living body, and may be a cell separated from, for example, a body fluid such as blood, a tissue, or a biopsy. The test cell may be, for example, an isolated cell, a cultured cell, or an established cell line. Alternatively, the cell may be a cell in a living body.

The test cell is, for example, a cell collected from a subject with a disease related to estrogen sensitivity. The disease is, for example, cancer. The test cell is, for example, a cell obtained from a lesion of a disease. In the case of cancer, the test cell is, for example, a breast cancer cell or an endometrial cancer cell. The test cell is preferably a cancer cell of a primary lesion or a metastatic lesion of cancer. In certain embodiment, the test cell is a cancer cell that have been found to be ER-positive.

Then, nucleic acid construct 1 is introduced into the test cell (introduction step S1). For example, when the test cell is a cell taken out of a living body, introduction step S1 can be performed by a known method such as a liposome method, a lipofection method, an electroporation method, a calcium phosphate co-precipitation method, a cationic polymer method, a microinjection method, a particle gun method, or a sonoporation method.

Particularly, the liposome method is preferably used. In the liposome method, nucleic acid construct 1 is encapsulated in a liposome (lipid particle), and a composition including the liposome is brought into contact with a cell. Thereby, the lipid particle is taken up into the cell by, for example, endocytosis, and the content is released into the cell. Details of the lipid particle are described in the following kit embodiments.

When the test cell is a cell in a living body, the introduction can be performed by injection or instilment of a composition including nucleic acid construct 1 into the living body. The composition may include, for example, the lipid particles including nucleic acid construct 1.

Then, estrogen 9 is added to the test cell (addition step S2). Estrogen 9 is a hormone that is a ligand of the ER and is estrone (E1), estradiol (E2), or estriol (E3). As used herein, estrogen 9 also includes derivatives of estrogen. The derivative is a compound in which a part of the molecule of estrogen 9 is changed, as long as it has a function as a ligand of ER. For example, the derivative also includes a precursor of E1, E2, or E3, a compound obtained from a chemical reaction of E1, E2, or E3.

As estrogen 9, commercially available products such as those manufactured by Sigma-Aldrich Co., LLC can be used. For example, powdered estrogen 9 is dissolved in an appropriate solvent and this solution is added to the test cell.

Then, the test cell is cultured (culture step S3). The culture may be performed by a known method suitable for the survival of the test cell, which is selected depending on the type of the test cell. For example, the culture temperature is preferably about 37° C., and the $CO_2$ concentration is preferably about 5%. In addition, the culture is preferably performed for 1 day to 3 days. The medium is a solid medium or a liquid medium, and a known medium suitable for survival of the test cell can be used.

Then, the activity of reporter protein 12 expressed from reporter gene 4 is detected (detection step S4). Detection step S4 may be performed in an extract obtained by extracting reporter protein 12 from the test cell or a supernatant of a culture solution of the test cell. Alternatively, detection step S4 can be performed on a live test cell.

When reporter protein 12 generates signal 13, the activity of reporter gene 4 can be detected by detecting the signal. Signal 13 is, for example, fluorescence, chemiluminescence, bioluminescence, biochemiluminescence, coloration, or the presentation of molecules such as proteins. Signal 13 may be emitted from reporter protein 12 itself, or may be generated by a reaction between reporter protein 12 and a specific substance (hereinafter, described as "first substance"), for example, an enzymatic reaction or binding.

For example, when reporter protein 12 is an enzyme, the first substance is a substrate thereof. For example, when reporter protein 12 is luciferase, the first substance is luciferin. Alternatively, signal 13 may be a signal derived from an additional detection reagent (hereinafter, described as a "second substance") for detecting the presence of a substance generated by the reaction between reporter protein 12 and the first substance.

For example, when the first substance and/or the second substance is used, these substances can be added to the test cell at the beginning of detection step S4. These substances may be added to the culture medium of the test cell or may be introduced into the cell. Alternatively, these substances may be added to an extract or a supernatant obtained from the test cell.

The detection of signal 13 may be performed by using any known method selected according to the type.

When reporter protein 12 is a fluorescent protein, signal 13 is obtained as fluorescence generated from the fluorescent protein by irradiating the cell with excitation light. The fluorescence (signal 13) can be detected by, for example, visual observation, a microscope, a flow cytometer, image analysis software, or a fluorometer.

When reporter protein 12 is luciferase, signal 13 is obtained as chemiluminescence by adding luciferin. The chemiluminescence (signal 13) can be detected by, for example, visual observation, a microscope, a flow cytometer, image analysis software, or a luminometer.

When reporter protein 12 is Q-galactosidase, signal 13 is obtained as the absorbance of the cell solution or extract by adding a substrate such as 5-burmo-4-chloro-3-indolyl-β-D-galactopyranoside (X-Gal) or o-nitrophenyl-β-D-galactopyranoside (ONPG). The absorbance (signal 13) can be detected by, for example, an absorptiometer, a spectrophotometer, or a turbidimeter.

When reporter protein 12 is nitric oxide synthase or xanthine oxidase, a substrate is added, and generated active oxygen is obtained as signal 13. Active oxygen (signal 13) can be detected by, for example, an electron spin resonance apparatus (ESR apparatus).

When reporter protein 12 is a heavy metal binding protein, a measurable heavy metal is added and the heavy metal bound to the reporter protein is obtained as signal 13. The heavy metal can be detected by a magnetic resonance imaging apparatus, a nuclear medicine diagnosis apparatus, an MRI imaging apparatus, or an X-ray computed tomography apparatus.

Then, estrogen-sensitive cell is discriminated from the detection result (information on the expression level of reporter protein 12) (discrimination step S5). For example, the intensity of signal 13 correlates with the expression level of reporter protein 12, and therefore a cell providing signal 13 and a cell having higher intensity of signal 13 than the threshold value can be determined to be an estrogen-sensitive cell having high activity of reporter gene 4 and high estrogen sensitivity. Conversely, a cell providing no signal 13 and a cell having lower intensity of signal 13 than the threshold value can be determined to be an estrogen insensitive cell having low estrogen sensitivity.

The threshold value can be, for example, a value of the expression level (intensity of signal 13) of reporter protein 12 obtained when the detection method of the embodiment is performed by using a cell known to have high estrogen sensitivity.

When reporter protein 12 is a drug resistant gene, culture step S4 may be performed by adding a corresponding drug to the culture medium. In this case, the test cell having high estrogen sensitivity can survive, and the test cell having low estrogen sensitivity can die. Thereby, estrogen-sensitive cell can be discriminated.

Alternatively, in detection step S4, reporter protein 12 may be directly detected or quantified instead of performing detection of signal 13 or screening with a drug. In this case, a cell with reporter protein 12 detected and a cell having higher quantitative value than the threshold value can be determined to be a cell having high activity of reporter gene 4 and high estrogen sensitivity.

Thus, estrogen-sensitive cell can be discriminated. For example, according to the method of the embodiment, when ER-positive breast cancer cells are used as the test cell, the ER-positive breast cancer cells can be further classified by estrogen sensitivity. In addition, according to the present method, it is possible to discriminate the estrogen-sensitive cell with higher sensitivity by using XRE sequence 6 in addition to ERE sequence 5. According to an embodiment, for example, it is possible to discriminate with about 1.4 times to several times higher sensitivity as compared with the case of ERE sequence 5 alone.

XRE sequence 6 generally promotes transcription of surrounding genes by binding of AhR bound to a ligand such as dioxin. However, according to the present method, XRE sequence 6 does not require that a ligand of AhR binds to AhR, and estrogen-sensitive cell can be discriminated.

In a further embodiment, the present method may further include a step of calculating an abundance ratio of the estrogen-sensitive cell. The abundance ratio of the estrogen-sensitive cell is obtained by measuring the number of the test cell (A) and the number of the estrogen-sensitive cell (B) and substituting these into the following equation (I).

$$\text{Abundance rate of estrogen-sensitive cell}=(B)/(A) \quad \text{Equation (I)}$$

The number of cells may be measured by a known method. For example, the number of cells may be measured visually by microscopic observation, or may be automatically measured from a microscopic image. Alternatively, flow cytometry may be used.

The cell number (B) is the number of the cell having high activity of reporter gene 4 in detection step S12. For example, the cell number (B) is the number of cells providing signal 13. When a drug resistance gene is used as reporter gene 4, the cell number (B) is the number of survived cells.

The cell number (A) of the test cell is, for example, the number of cells detected by irradiating the test cell with scattered light. When a drug resistance gene is used, the cell number (A) of the test cell may be measured before introduction step S11.

The abundance ratio of the estrogen-sensitive cell does not need to be calculated for all of the test cells, and may be calculated for a part of the sampled test cells or a part of the test cells in the field of view of the microscope, and the abundance ratio of the estrogen-sensitive cell of all test cells may be estimated from the result.

In addition, the intensity of estrogen sensitivity of all test cells may be determined by using the abundance ratio. It can be determined that the intensity of estrogen sensitivity is higher with higher abundance ratio of the estrogen-sensitive cell. The intensity of estrogen sensitivity may be determined by previously preparing a calibration curve or a threshold value representing the relationship between the abundance ratio and the intensity with using a cell group having known intensity of estrogen sensitivity, and then using the calibration curve or the threshold value as a reference.

In addition, the detection result may be further corrected. For example, although estrogen 9 is not added, the activity of reporter gene 4 may be detected. Therefore, the detection result can be corrected by comparing the detection value of reporter protein 12 in the case with the addition of estrogen 9 (E(+)) with the detection value of reporter protein 12 in the case without the addition of estrogen 9 (E(−)). The detection value of E(+) is obtained by performing the present detection method. The detection value of E(−) is obtained from the step excluding addition step S2 of the present detection method. The detection value can be corrected by, for example, the following equation (II-1).

$$\text{Corrected value of detection value}=E(+)/E(-) \qquad \text{Equation (II-1)}$$

Discrimination step S5 may be performed based on the corrected detection result.

Alternatively, the abundance ratio may be corrected by using the below equation instead of the detection value. That is, the corrected value of the abundance ratio is obtained by the following equation (II-2).

$$\text{Corrected value of abundance ratio}=\text{abundance ratio in the case of } E(+)/\text{abundance ratio in the case of } E(-) \qquad \text{Equation (II-2)}$$

The corrected abundance ratio may be used for determining the intensity of estrogen sensitivity.

According to the method for detecting estrogen sensitivity described above, by using nucleic acid construct 1 of the embodiment, the estrogen-sensitive cell can be discriminated more sensitively, and the intensity of estrogen sensitivity can be determined.

In one embodiment, step from S1 to S5 may be continuously carried out without performing another step between any of these steps.

Therapeutic Effect Prediction Method

According to a further embodiment, the detection result (information on the expression level of reporter protein 12) obtained in detection step S3 can be used to predict the efficacy of hormone treatment for the cancer in a subject using nucleic acid construct 1. Herein, "hormone treatment" is a treatment by administration of a drug that suppresses the action of estrogen. Hereinafter, a therapeutic effect of predicting method according to an embodiment will be described. The present method includes, for example, the following, as shown in FIG. 5. (S11) an introduction step of introducing a nucleic acid construct into a test cell obtained from a subject; (S12) an addition step of adding estrogen to the test cell; (S13) a culture step of culturing the test cell; (S14) a detection step of detecting an activity of a reporter protein expressed from a reporter gene; and (S15) a prediction step of predicting the efficacy of hormone treatment for the subject from the result of the detection step.

First, the test cell is collected from a subject. In the present method, the test cell is a cancer cell, for example, a breast cancer cell or an endometrial cancer cell, and is preferably an ER-positive breast cancer cell.

Introduction step S11 to detection step S13 can be performed in the same manner as the introduction step S1 to the detection step S3.

In prediction step S15, when nucleic acid construct 1 is introduced and reporter protein 12 is expressed or expressed at a level higher than the threshold value (the activity of reporter gene 4 is high), it can be predicted that hormone treatment is effective for the cancer of the subject from which the test cell is collected. In contrast, when reporter protein 12 is not expressed or is expressed at a low level (the activity of reporter gene 4 is low), it can be predicted that hormone treatment is not effective for cancer in a subject.

Prediction step S15 may be performed based on the abundance ratio. It can be predicted that the hormone therapy is more effective as the abundance ratio is higher. The prediction of the therapeutic effect may be performed based on a threshold value of the abundance ratio. For example, the threshold of the abundance ratio is 10% or more, and when the abundance ratio is higher than this, it is also possible to determine that the hormone treatment is effective.

Information on the expression level of reporter protein 12 or information on the abundance ratio of the estrogen-sensitive cell can also be used to determine the schedule of the hormone treatment, for example, the dose, the number of doses, or the type of combination treatment. For example, these conditions of the drug may be changed according to the abundance ratio.

In one embodiment, step from S11 to S15 may be continuously carried out without performing another step between any of these steps.

CMOS Image Sensor

Figure 6:
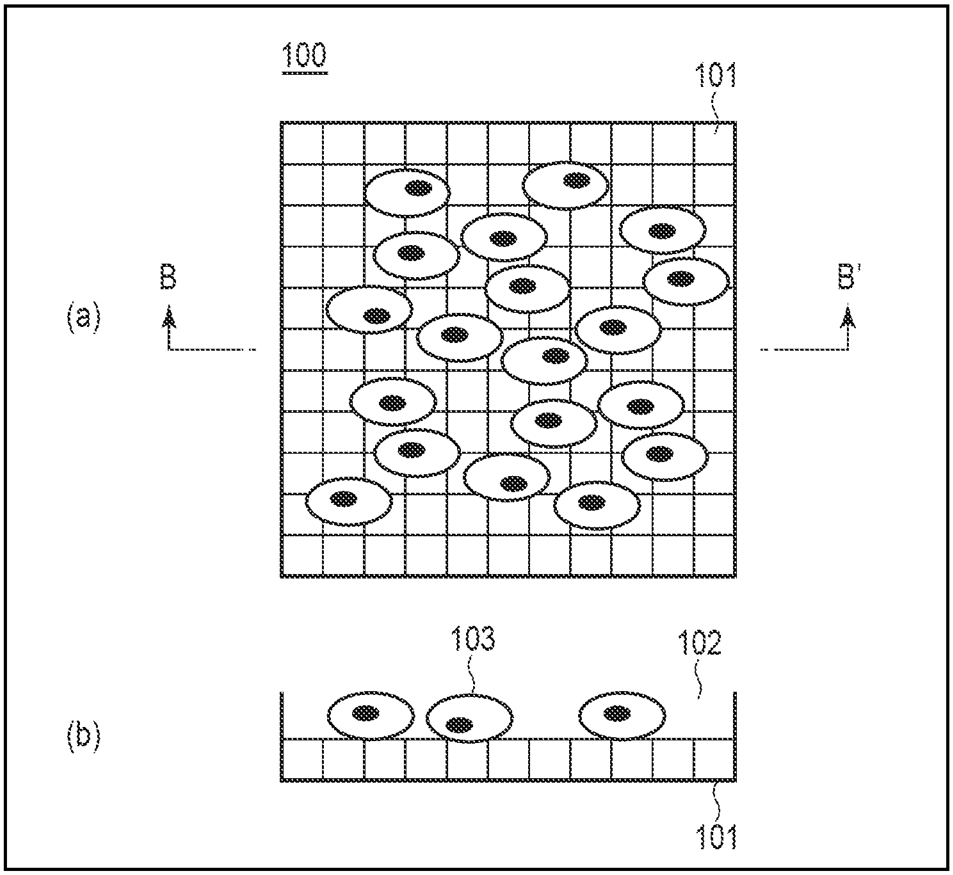
FIG. 6 is a plan view and a cross-sectional view showing an example of the CMOS image sensor of the embodiment.

In the method for detecting the estrogen-sensitive cell and the method for predicting the therapeutic effect according to the embodiment, the culture step and the detection step may be performed on a CMOS image sensor. FIG. 6 illustrates a state when CMOS image sensor 100 is used. Part (a) of FIG. 6 illustrates a plan view of CMOS image sensor 100, and Part (b) of FIG. 6 illustrates a cross-sectional view taken along line B-B' of Part (a) of FIG. 6. CMOS image sensor 100 includes a plurality of sensing section 101 arranged in a matrix in a two-dimensional region, and sample accommodation section 102 provided on the plurality of sensing section 101. Test cell 103 can be cultured in the sample accommodation section 102. Each sensing section 101 is an optical sensor, and can two-dimensionally detect the presence or absence of test cell 103 on sensing section 101 and signal 13 generated from test cell 103 or the culture medium.

Kit

According to the embodiment, there is provided a kit used for detecting the estrogen-sensitive cell or predicting the effect of the hormone treatment for the cancer in a subject.

The kit includes nucleic acid construct 1. Nucleic acid construct 1 is provided, for example, as a composition included in a solvent. Examples of the solvent include endotoxin-free water, PBS, TE buffer, or HEPES buffer. The composition may further include an excipient, a stabilizer, a diluent, and/or an auxiliary, etc.

Figure 7:
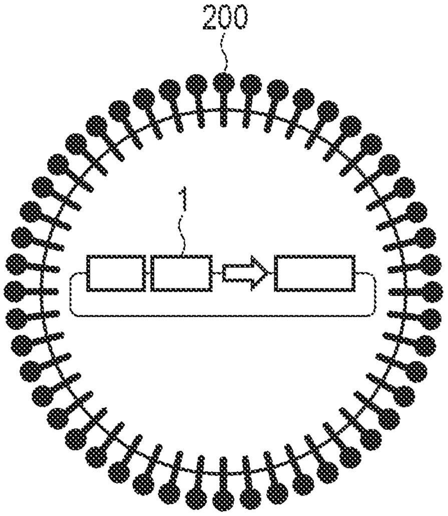
FIG. 7 is a cross-sectional view showing an example of a lipid particle encapsulating the nucleic acid construct of the embodiment.

Nucleic acid construct 1 is preferably included in the kit in a state of being encapsulated in the lipid particle. The lipid particle is described with reference to FIG. 7. As shown in FIG. 7, lipid particle 200 is a hollow spherical lipid membrane.

The lipid membrane constituting lipid particle 200 is a lipid membrane such as a monolayer, a lipid bilayer, or a lipid triple layer. In addition, lipid particle 200 may have a multilayer structure in which a plurality of lipid membranes are further overlapped.

Lipid particle 200 may include one lipid material; however, preferably includes a plurality of lipid materials. The lipid material preferably includes, for example, at least a base lipid exemplified below, the first lipid compound, and the second lipid compound.

The base lipid is preferably a phospholipid or a sphingolipid, for example, diacylphosphatidylcholine, diacylphosphatidylethanolamine, ceramide, sphingomyelin, dihydrosphingomyelin, kephalin, cerebroside, or a combination thereof. The base lipid may be, for example, a lipid of a main component of a biological membrane, or may be an artificially synthesized lipid.

As the base lipid, particularly, a cationic lipid or neutral lipid is preferably used, and the acid dissociation constant of lipid particle 200 can be adjusted by the content thereof. It is preferable to use 1,2-dioleoyl-3-trimethylammonium propane (DOTAP) as the cationic lipid, and it is preferable to use 1,2-dioleoyl-sn-glycero-3-phosphoethanolamine (DOPE) as the neutral lipid.

The base lipid is preferably included at 30% to about 80% (molar ratio) of the total lipid material. Alternatively, nearly 100% of the total lipid material may be constituted from base lipids.

The first lipid compound and the second lipid compound are biodegradable lipids. The first lipid compound can be represented by the formula Q-$CHR_2$. (In the formula, Q is a nitrogen-containing aliphatic group including two or more tertiary nitrogen and no oxygen, Rs are each independently an aliphatic group of $C_{12}$ to $C_{24}$, and at least one of Rs includes a linking group LR selected from the group consisting of —C(═O)—O—, —O—C(═O)—, —O—C(═O)—O—, —S—C(═O)—, —C(═O)—S—, —C(═O)—NH—, and —NHC(═O)— in the main chain or side chain thereof).

When lipid particle 200 includes the first lipid compound, the surface of lipid particle 200 is non-cationic, and therefore the disorder in cell introduction is reduced, allowing enhancement of the introduction efficiency of the content encapsulated.

As the first lipid compound, for example, a lipid having a structure represented by the following formula is preferably used because the introduction efficiency is more excellent. Particularly, it is preferable to use a lipid compound of the following formula (1-01) and/or a lipid compound of the following formula (1-02).

(1-01)

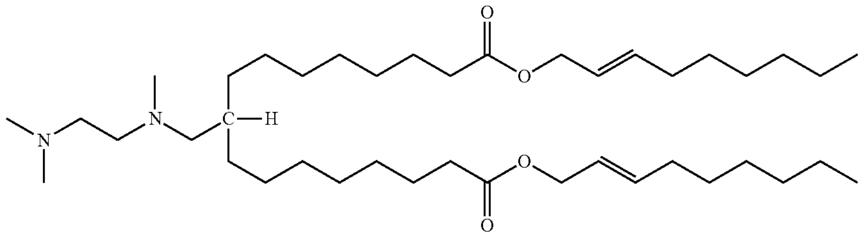

(1-02)

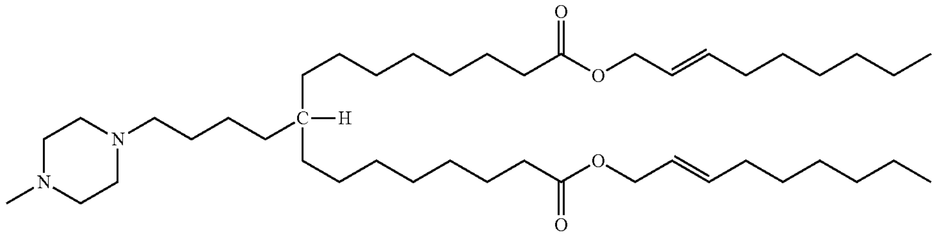

The second lipid compound can be represented by the formula P—[X—W—Y—W'—Z]$_2$ (In the formula, P is an alkyleneoxy including one or more ether bonds in the main chain, Xs are each independently a divalent linking group including a tertiary amine structure, Ws are each independently a $C_1$ to $C_6$ alkylene, Ys are each independently a divalent linking group selected from the group consisting of a single bond, an ether bond, a carboxylic acid ester bond, a thiocarboxylic acid ester bond, a thioester bond, an amide bond, a carbamate bond, and a urea bond, W's are each independently a single bond or a $C_1$ to $C_6$ alkylene, and Zs are each independently a fat-soluble vitamin residue, a sterol residue, or a $C_{12}$ to $C_{22}$ aliphatic hydrocarbon group).

When the second lipid compound is included, the amount of nucleic acid construct 1 encapsulated in lipid particle 200 can be increased.

For example, use of the second lipid compound having the following structure is preferable because the amount of nucleic acid construct 1 encapsulated is more excellent. Particularly, it is preferable to use a compound of the following formula (2-01).

(2-01)

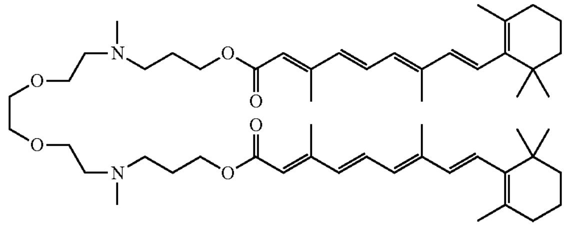

When lipid particles 200 including the first and second lipid compounds described above are used, it is possible to increase the amount of nucleic acid construct 1 encapsulated and to enhance the introduction efficiency of nucleic acid construct 1 into the test cell. In addition, cell death of the introduced test cells can be reduced.

The first and second lipid compounds are preferably included at about 20% to about 70% (molar ratio) with respect to the total lipid materials.

It is also preferable that the lipid material includes a lipid that prevents aggregation of lipid particles 200, such as polyethylene glycol (PEG) dimyristoyl glycerol (DMG-PEG). Such a lipid is preferably included at about 1% to about 5% (molar ratio) with respect to the total lipid materials of lipid particle 200.

Lipid materials may further include a lipid such as a relatively less toxic lipid for modulating toxicity, a lipid having the functional group that binds ligand to lipid particle 200, a lipid for suppressing leakage of a content encapsulated such as sterol, for example, cholesterol. Particularly, cholesterol is preferably included.

The type and composition of the lipid to be used are appropriately selected in consideration of the intended acid dissociation constant (pKa) of the lipid particle 200, the size of lipid particle 200, the type of the content encapsulated, or stability in the test cell to be introduced.

For example, lipid particle 200 preferably includes a compound of Formula (1-01) or Formula (1-02) and/or a compound of Formula (2-01), DOPE and/or DOTAP, cholesterol, and DMG-PEG.

Lipid particle 200 can be produced by using a known method used when a small molecule is enclosed in lipid particle 200, for example, a Bangam method, an organic solvent extraction method, a surfactant removal method, or a freeze-thaw method. For example, a lipid mixture obtained by including the material of lipid particles 200 in an organic solvent such as alcohol at a desired ratio and an aqueous buffer including a component to be included such as a vector are prepared, and the aqueous buffer is added to the lipid mixture. The obtained mixture is stirred and suspended to be formed into lipid particles 200 encapsulating the vector or the like.

In addition, the kit may further include a reagent for detecting reporter protein 12. The reagent is, for example, the first substance and/or the second substance described in detection step S4.

The kit may further include estrogen 9 used in the addition step.

EXAMPLE

Hereinafter, examples of producing and using the vector of the embodiment will be described.

Example 1: Preparation of Reporter Vector for Detecting Activated Estrogen Receptor (ER)

First, there was prepared vector A containing an ampicillin resistance gene sequence, a ColE1 origin sequence, a SV40 origin sequence, a SV40 poly-A sequence, a gene encoding NanoLuc® luciferase (hereinafter, referred to as "NanoLuc gene"), and a BGH poly-A sequence. A restriction enzyme treatment was performed at the SacI site and the XhoI site located upstream of the NanoLuc gene, then 0.8% agarose electrophoresis was performed, and the fragment of the vector A was purified from the gel.

The artificially synthesized sequence (SEQ ID NO. 11) shown in Table 6 was used as a template, primer sets (1) to (5) shown in Table 7 were used respectively, and whereby the amplification was performed by a PCR method under the conditions shown in Table 8.

TABLE 6

| Artificial synthetic sequence (SEQ ID NO: 11) |
|---|
| tatcgataggtaccgagctcgctccgaattcggctccgaattcgcccttcaggtccgaggttc<br>tagacgagtttacttggaggtcattatgaccacgatgtcgagtttacatgcgcggtcagagtg<br>accacgtatgtcgagtttactcccacggtcatgatgaccacgtatgtcgagtttacttggttg<br>gtcagattgaccacgtatgtcgagtttataattcggtcatttcgaccacgtatgtcgagttta<br>ctttcacggtcaggatgaccacgtatgtcgaggtaggcgtgtacggtgggaggcctatataag<br>cagagctcgtttagtgaaccgtcagatcgcaaagggcgaattcgaccgaattcgacCTCGAGa<br>tctgcgatc |

The underline represents the ERE sequence and the double underline represents the promoter sequence.

TABLE 7

| Primer set | | | |
|---|---|---|---|
| | Primer | SEQ ID NO | Sequence |
| (1) | Forward | 12 | tatcgataggtaccgagctc |
| | Reverse | 13 | GATCGCAGATCTCGAG |
| (2) | Forward | 14 | tatcgataggtaccgagctcgatatcTGTCTTCATGTCGTGTCTAGGGCGG<br>ttctagacgagtttacttggaggt |
| | Reverse | 13 | GATCGCAGATCTCGAG |

TABLE 7-continued

| Primer set | | | |
|---|---|---|---|
| | Primer | SEQ ID NO | Sequence |
| (3) | Forward | 12 | tatcgataggtaccgagctc |
| | Reverse | 15 | GATCGCAGATCTCGAGGCGATCTGACGGTTCACTAAACGAGCTCTGCTTAT ATAGGCCTCCCACCGTACACGCCTACCGTCGAATTCGGCCGCCCTAGACAC GACATGAAGACATCGACATACGTGGTCATCCTGACC |
| (4) | Forward | 14 | tatcgataggtaccgagctcgatatcTGTCTTCATGTCGTGTCTAGGGCGG ttctagacgagtttacttggaggt |
| | Reverse | 15 | GATCGCAGATCTCGAGGCGATCTGACGGTTCACTAAACGAGCTCTGCTTAT ATAGGCCTCCCACCGTACACGCCTACCGTCGAATTCGGCCGCCCTAGACAC GACATGAAGACATCGACATACCTGGTCATCCTGACC |
| (5) | Forward | 16 | tatcgataggtaccgagctcTGTCTTCATGTCGTGTCTAGGGCGGacgtat gtcgaggtaggcgtgtac |
| | Reverse | 13 | GATCGCAGATCTCGAG |

The underline represents the XRE sequence (SEQ ID NO. 8).

TABLE 8

| PCR amplification condition | | |
|---|---|---|
| Temperature | Time | |
| 98° C. | 3 min. | |
| 98° C. | 10 sec. | |
| 60° C. | 15 sec. | 30 cycle |
| 68° C. | 1 min. | |
| 68° C. | 10 min. | |
| 4° C. | ∞ | |

The amplification yielded five artificial DNAs (1) to (5), respectively, with the following sequence placed in front of the promoter sequence, corresponding to the promoters (1) to (5): (1) ERE sequence; (2) XRE sequence-ERE sequence; (3) ERE sequence-XRE sequence; (4) ERE sequence-XRE sequence-ERE sequence; and (5) XRE sequence.

(As the XRE sequence, one having the base sequence of SEQ ID NO. 8 was used.)

Figure 10:
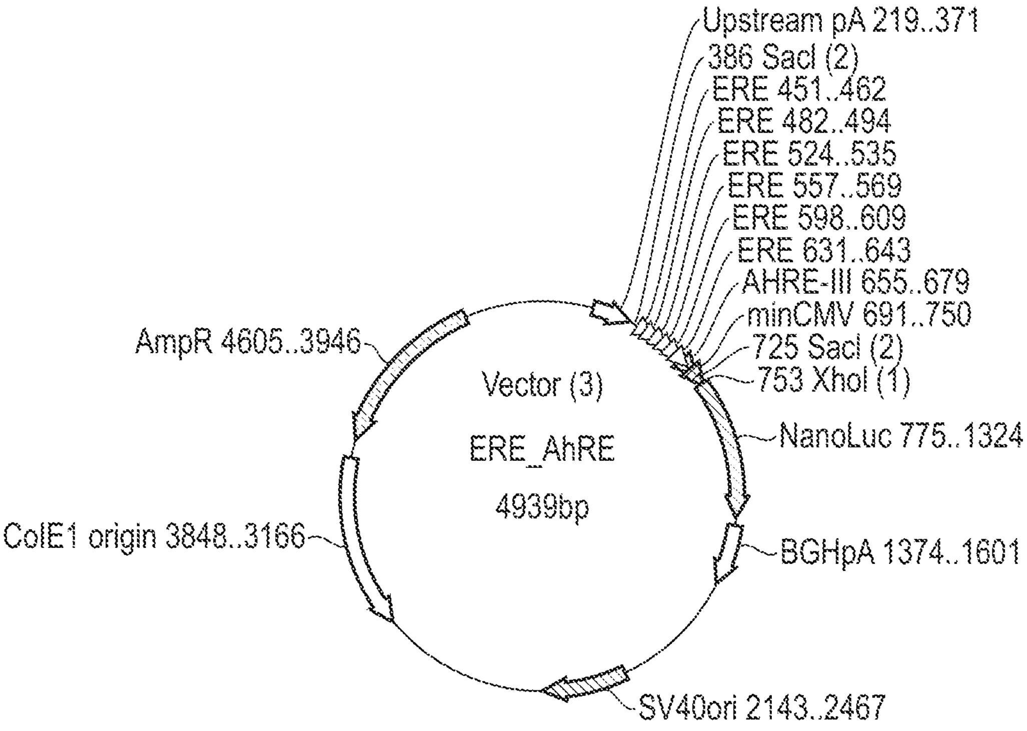
FIG. 10 is a view showing vector (3) produced in Example 1.
Figure 11:
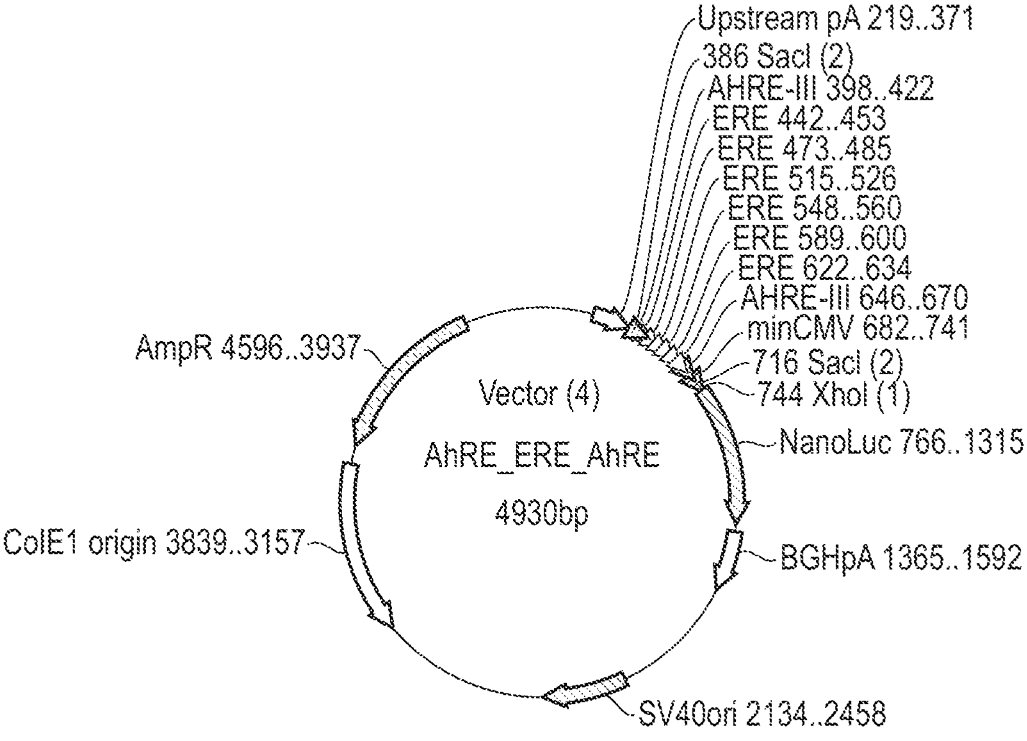
FIG. 11 is a view showing vector (4) produced in Example 1.
Figure 12:
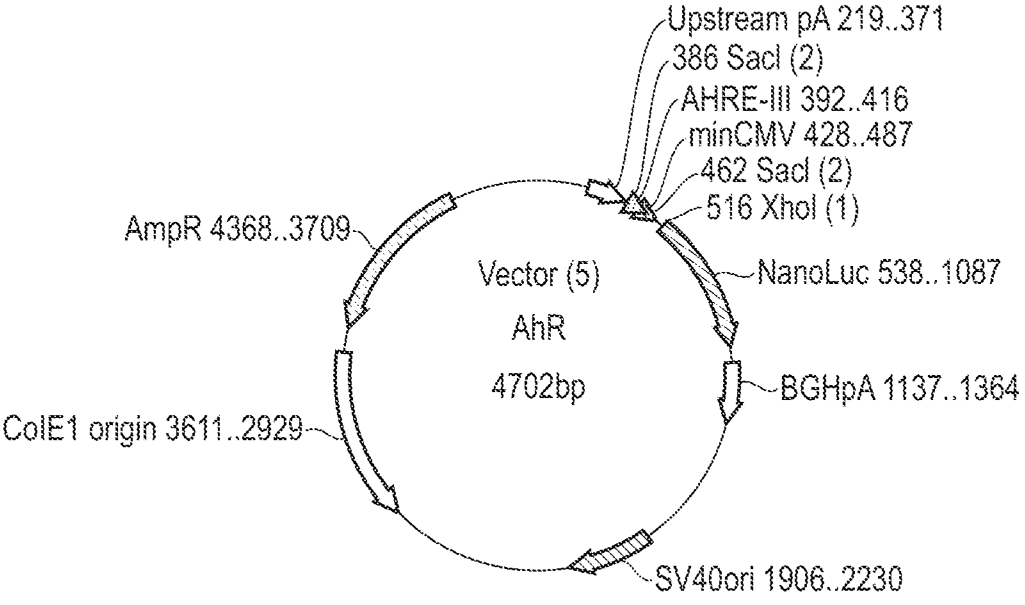
FIG. 12 is a view showing vector (5) produced in Example 1.

The amplification product was purified by 0.8% agarose electrophoresis and ligated to the SacI/XhoI site of vector A by using a cloning kit (In-Fusion®, TaKaRa BiO Inc.). As a result, there were obtained vector (1) including artificial DNA (1) shown in FIG. 8, vector (2) including artificial DNA (2) shown in FIG. 9, vector (3) including artificial DNA (3) shown in FIG. 10, vector (4) including artificial DNA (4) shown in FIG. 11, and vector (5) including artificial DNA (5) shown in FIG. 12. The XRE sequence of SEQ ID NO. 8 is described as "AhRE" or "AhRE-III" in the figure. Vectors (1) to (5) were subjected to DNA sequence analysis to confirm that these vectors had intended sequences.

Example 2: Preparation of Lipid Particles Encapsulating an Activated Estrogen Receptor (ER)-Detecting Reporter Vector A cationic peptide was added to a DNA solution including each of vectors (1) to (5) prepared in Example 1 to form a DNA-peptide condensate. Then this condensate was added to a solution of lipid (FFT10 (lipid compound of the formula (1-01))/SST04 (lipid compound of the formula (2-01))/DOTAP/DOPE/cholesterol/PEG-DMG=37/15/10.5/10.5/30/2 mol) dissolved in ethanol. 10 mM HEPES (pH 7.3) was gently added to the resultant mixed solution, and then the mixture was washed and concentrated by centrifugal ultrafiltration to provide lipid particles including vectors (1) to (5). The DNA encapsulation amount of the lipid particles was measured by a DNA quantification kit (Quant-iT™ PicoGreen™ dsDNA Assay Kit, manufactured by Thermo Fisher Scientific Inc.).

Example 3: Introduction of Activated Estrogen Receptor (ER)-Detecting Reporter Vector into Cell Line Introduction into Human Mammary Tumor-Derived Cell Line A human mammary tumor-derived cell line (MCF-7) was subjected to adhesion culture in a culture flask at 37° C. in a 5% $CO_2$ atmosphere using a medium (MEM, GIBCO) supplemented with 10% fetal bovine serum (FBS). After the culturing, the medium was removed, the cells were washed with PBS, and then the cells were detached from culture flask by 0.25% Trypsin-EDTA treatment. Then, the cells were suspended in the media including 10% FBS to inactivate Trypsin. After the cells were collected by centrifugation, the cells were suspended in the medium including 10% FBS so as to have $2.0 \times 10^5$ cells/mL. 200 μL of the cell suspension was added to a 96 well culture dish (manufactured by Thermo Fisher Scientific Inc.) so as to provide $4.0 \times 10^4$ cells/well. Thereafter, the DNA-encapsulating lipid particle prepared in Example 2 was added to the well so as to provide 65 ng/well of the DNA, and culturing was performed in an atmosphere of 37° C. and 5% $CO_2$. The culturing was performed in an atmosphere at 37° C. and 5% $CO_2$ for 15 minutes, then estradiol (E2, manufactured by Sigma-Aldrich Co., LLC), a substrate for ER, was added so that the final concentration was 4 nM, and culture was performed in an atmosphere at 37° C. and 5% $CO_2$.

Measurement of Expression Level of NanoLuc (NanoLuc Luminescence Assay)

24 hours after the addition of the DNA-encapsulating lipid particles, the culture plate was taken out of the incubator, and the medium was removed. Thereafter, the cells were washed with PBS, 100 μL/well of GloLysisBuffer (Promega Corporation) was added thereto, and the resultant mixed solution was frozen at −80° C. for 30 minutes. The frozen solution was melted at room temperature, and then the cell lysate was collected in a 1.5 ml centrifuge tube. Centrifugation was performed at 15000 rpm for 10 minutes to precipitate the cell residue, and 25 μL of the supernatant was dispensed into a 96 well plate (Black, Nunc). To the dispensed supernatant, 25 μL of a luciferase substrate solution included in a luciferase assay system (Nano-Glo® Luciferase Assay System, Promega Corporation) was added and mixed. The luminescence intensity (RLU) per 1 well per 0.1 seconds of the obtained mixed solution was measured by using a luminometer (Infinite F200 Pro, Tecan Group Ltd.).

The luminescence intensity was also measured when E2 was not added. The corrected value (E2(+)/(−)) was calculated by dividing the value in the case of adding E2, (E2(+)), by the value in the case of not adding E2, (E2 (−)).

Comparative Results of Promoter Activity

Figure 13:
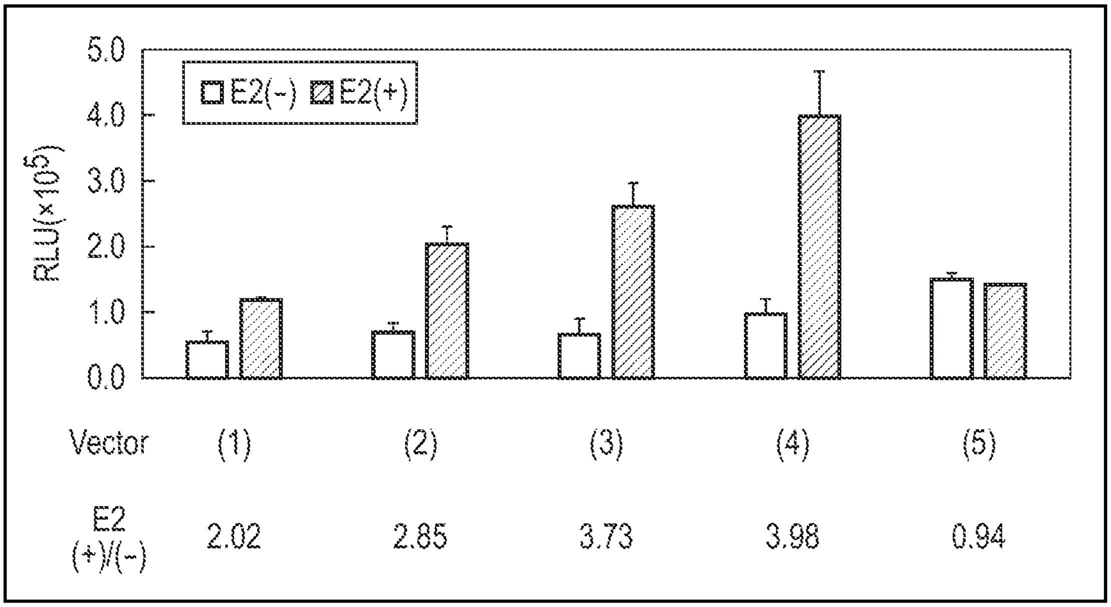
FIG. 13 is a graph showing the experimental result in Example 3.

FIG. 13 shows the measurement results of the luminescence intensity (RLU). The corrected values of the RLU values were 2.02 for vector (1) (ERE sequence only), 2.85 for vector (2) (XRE sequence-ERE sequence), 3.73 for vector (3) (ERE sequence-XRE sequence), 3.98 for vector (4) (XRE sequence-ERE sequence-XRE sequence), and 0.94 for vector (5) (XRE sequence only).

Vectors additionally including the XRE sequences had higher luminescence intensity than vectors including only the ERE sequences. In addition, the magnitude of the intensity was in the order of the ERE sequence only<the XRE sequence-the ERE sequence<the ERE sequence-the XRE sequence<the XRE sequence-the ERE sequence-the XRE sequence. In addition, the vector including only the XRE sequence had almost no difference between E2(+) and E2(−), and failed to detect the activated estrogen receptor (ER).

These results have found that the detection sensitivity of the activated estrogen receptor (ER) is improved in using the vector including both the ERE sequence and the XRE sequence.

Example 4: Evaluation of Liposome Method

Introduction into Human Mammary Tumor-Derived Cell Line

A human mammary tumor-derived cell line (MCF-7) was subjected to adhesion culture in a culture flask at 37° C. in a 5% $CO_2$ atmosphere using a medium (MEM, GIBCO) supplemented with 10% fetal bovine serum (FBS). After the culturing, the medium was removed, the cells were washed with PBS, and then the cells were detached from culture flask by 0.25% Trypsin-EDTA treatment. Then, the cells were suspended in the media including 10% FBS to inactivate Trypsin. After the cells were collected by centrifugation, the cells were suspended in the medium including 10% FBS so as to have $2.0\times10^5$ cells/mL. 200 μL of the cell suspension was added to a 96 well culture dish (manufactured by Thermo Fisher Scientific Inc.) so as to provide $4.0\times10^4$ cells/well.

Introduction of DNA into Cells by Lipofectamine 3000

Vectors (2) to (4) prepared in Example 1 were introduced into a human mammary tumor-derived cell line (MCF-7) by using Lipofectamine 3000 reagent (manufactured by Invitrogen corporation). The introduction was performed according to the manufacturer's instruction. Vectors (2) to (4) were added to the wells so as to provide 65 ng/well, and cultured in an atmosphere of 37° C. and 5% $CO_2$ for 15 minutes. Thereafter, estradiol (E2, manufactured by Sigma-Aldrich Co., LLC), a substrate of ER, was added so that the final concentration was 4 nM, and culturing was performed in an atmosphere of 37° C. and 5% $CO_2$.

Measurement of Expression Level of NanoLuc (NanoLuc Luminescence Assay)

48 hours after vectors (2) to (4) were added by Lipofectamine 3000, the culture plate was removed from the incubator, and the medium was removed. Thereafter, the cells were washed with PBS, 100 μL/well of GloLysisBuffer (Promega Corporation) was added thereto, and the resultant mixed solution was frozen at −80° C. for 30 minutes. The frozen solution was melted at room temperature, and then the cell lysate was collected in a 1.5 ml centrifuge tube. Centrifugation was performed at 15000 rpm for 10 minutes to precipitate the cell residue, and 25 μL of the supernatant was dispensed into a 96 well plate (Black, Nunc). To the dispensed supernatant, 25 μL of a luciferase substrate solution included in a luciferase assay system (Nano-Glo® Luciferase Assay System, Promega Corporation) was added and mixed. The luminescence intensity (RLU) per 1 well per 0.1 seconds of the obtained mixed solution was measured by using a luminometer (Infinite F200 Pro, Tecan Group Inc.). In addition, the corrected value E2(+)/(−) was calculated in the same manner as in Example 3.

Comparative Results of Promoter Activity

Figure 14:
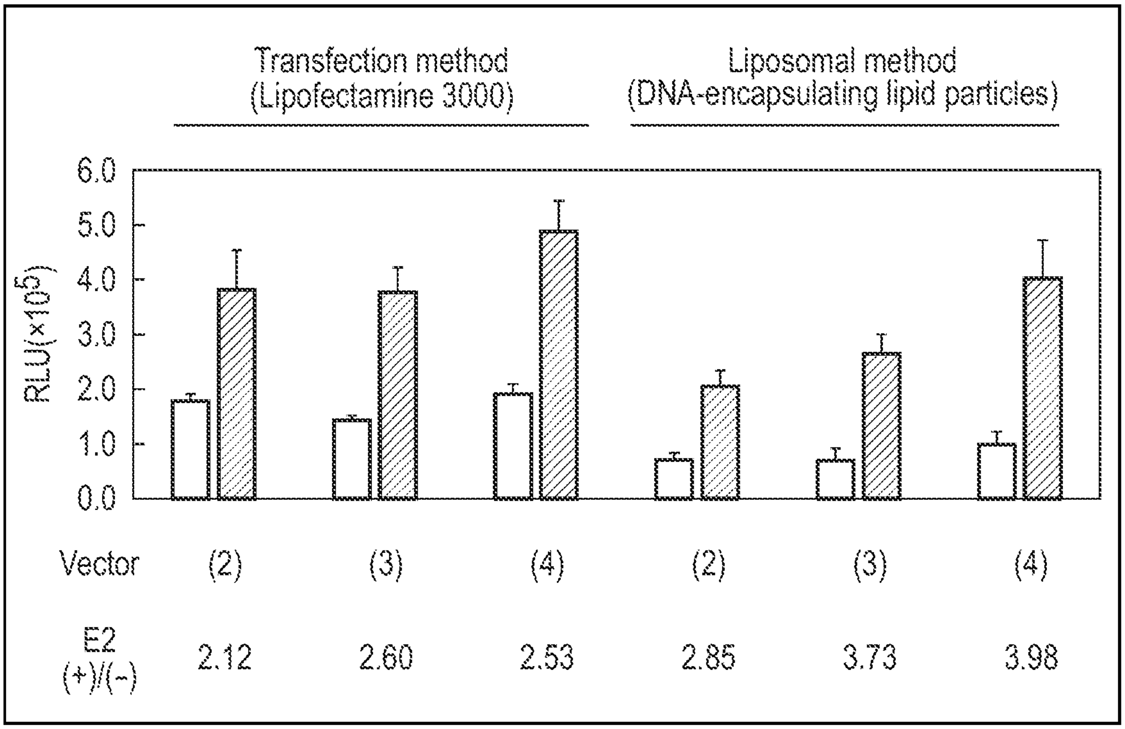
FIG. 14 is a graph showing the experimental result in Example 4.

FIG. 14 shows the measurement results of the luminescence intensity (RLU) when the Lipofectamine 3000 reagent was used. The corrected values of the RLU values were 2.12 for vector (2) (XRE sequence-ERE sequence), 2.60 for vector (3) (ERE sequence-XRE sequence), and 2.53 for vector (4) (XRE sequence-ERE sequence-XRE sequence).

The above results were compared with the corrected values of vectors (2) to (4) of the embodiment of the luminescence intensity (RLU) in the case of using the lipid particles obtained in Example 3.

The corrected values of the RLU values in the case of using lipid particles were 2.85 for vector (2) (XRE sequence-ERE sequence), 3.73 for vector (3) (ERE sequence-XRE sequence), and 3.98 for vector (4) (XRE sequence-ERE sequence-XRE sequence).

When the Lipofectamine 3000 reagent was used, the corrected value was lower than that when the lipid particles were used. Therefore, it has been found that detection sensitivity is further improved by using lipid particles.

Example 5: Comparison of XRE Sequences

There were prepared a vector using AhRE-III (SEQ ID NO. 8) as an XRE sequence and a vector using GCGTG as an XRE sequence. The configuration of the enhancer sequences of both vectors was an ERE sequence-XRE sequence. Both vectors were introduced into a human mammary tumor-derived cell line in the same manner as in Example 3, the NanoLuc luminescence intensity was measured under the condition of E2(+) or E2(−), and the corrected value, E2(+)/(−), was calculated.

Figure 15:
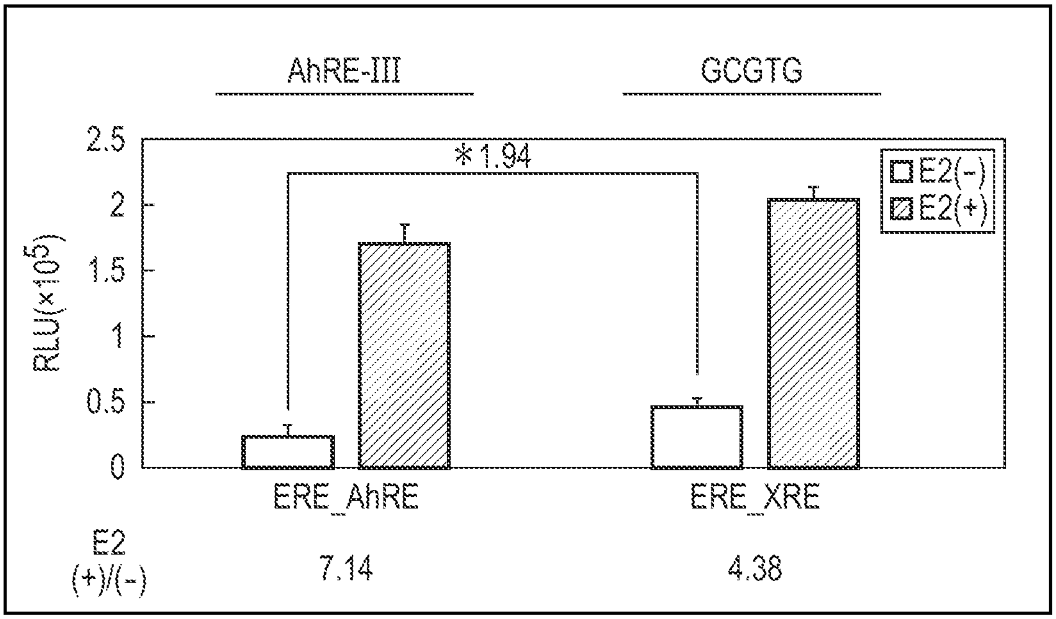
FIG. 15 is a graph showing the experimental result in Example 5.
Figure 16:
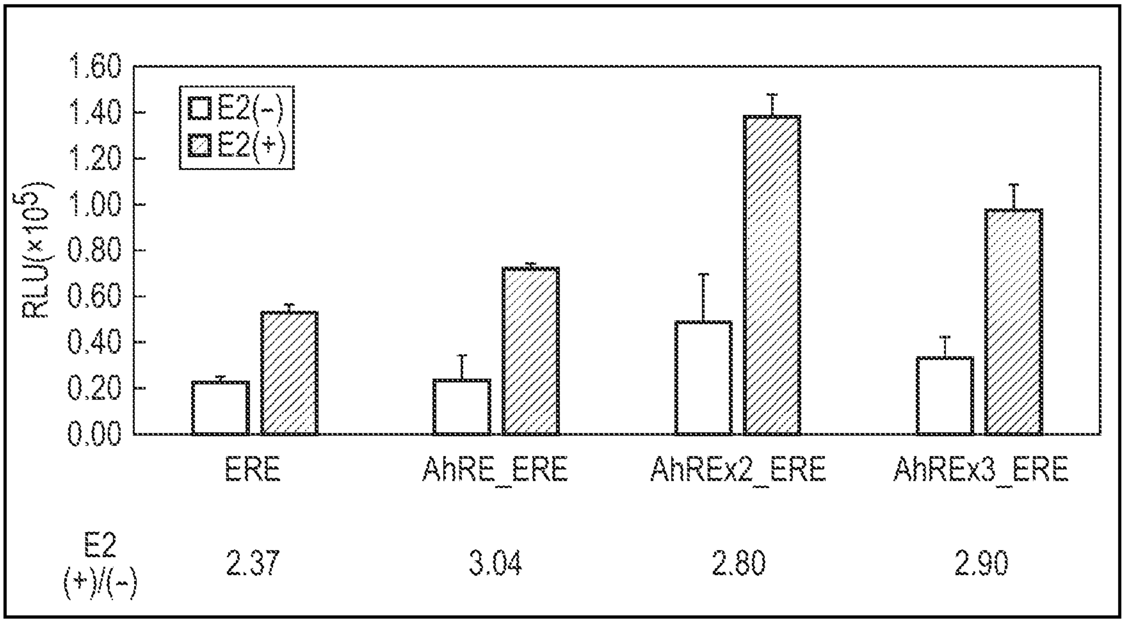
FIG. 16 is a graph showing the experimental result in Example 6.

The results are shown in FIG. 15. E2(+)/(−) was a higher value of 7.14 in the vector using AhRE-III (SEQ ID NO. 8), and a lower value of 4.38 in the vector using GCGTG. In addition, E2(−) was significantly smaller in AhRE-III (SEQ ID NO. 8). In the figure, "*" is a value of GCGTG when E(−) of AhRE-III is set to "1". Therefore, it has been found that the detection sensitivity is further improved when AhRE-III is used.

Example 6: Evaluation of Enhancer Sequences Including a Plurality of AhRE-III There were prepared a vector (ERE) including an ERE sequence as an enhancer sequence, a vector (AhRE_ERE)

including an AhRE and an ERE sequence, a vector (AhREx2_ERE) including two AhREs and an ERE sequence, and a vector (AhREx3_ERE) including three XRE sequences (AhRE) and an ERE sequence. Each of vectors were introduced into a human mammary tumor-derived cell line in the same manner as in Example 3, the NanoLuc luminescence intensity was measured under the condition of E2(+) or E2(−), and the corrected value, E2(+)/(−), was calculated.

E2(+)/(−) was 2.37 for the vector of ERE, 3.04 for the vector of AhRE_ERE, 2.80 for the vector of AhREx2_ERE, and 2.90 for the vector of AhREx3_ERE. Therefore, it has been found that the detection sensitivity is further improved in the case where a plurality of AhREs are ligated as compared with the case where only ERE is connected. When a plurality of AhREs were ligated, the value of E2(−) was increased as compared with the AhRE singly; however, the value of E2(+) was improved and the reactivity was excellent.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nucleic acid construct for detecting an estrogen-sensitive cell, comprising:

an enhancer sequence including at least an ERE sequence and at least a XRE sequence;

a promoter sequence ligated to downstream of the enhancer sequence; and a reporter gene ligated to downstream of the promoter sequence.

2. The nucleic acid construct according to claim 1, wherein the enhancer sequence comprises the ERE sequence and the XRE sequences ligated to upstream and downstream of the XRE sequence.

3. The nucleic acid construct according to claim 1, wherein the ERE sequence includes at least a base sequence of SEQ ID NO. 1 to 6.

4. The nucleic acid construct according to claim 3, wherein the ERE sequence includes the base sequence of SEQ ID NO. 1 to 6 in this order.

5. The nucleic acid construct according to claim 1, wherein the XRE sequence includes at least a base sequence of SEQ ID NO. 8.

6. The nucleic acid construct according to claim 1, wherein an expression promoter sequence is a virus-derived promoter or a mammary tissue-specific promoter.

7. The nucleic acid construct according to claim 1, wherein the reporter gene is a fluorescent protein gene, a luminescent protein gene, an active oxygen producing gene, or a drug resistance gene.

8. The nucleic acid construct according to claim 1, wherein the test cell is a cancer cell.

9. The nucleic acid construct according to claim 8, wherein the cancer cell is a breast cancer cell or an endometrial cancer cell.

10. A kit for detecting estrogen-sensitive cells, comprising a nucleic acid construct encapsulated in a lipid particle, the nucleic acid construct including:

an enhancer sequence including at least an ERE sequence and at least an XRE sequence;

a promoter sequence ligated to downstream of the enhancer sequence; and a reporter gene ligated to downstream of the promoter sequence.

11. The kit according to claim 10, wherein the lipid particle includes a compound of the following formula (1-01), a compound of following formula (1-02), and/or a compound of following formula (2-01) as a material thereof:

(1-01)

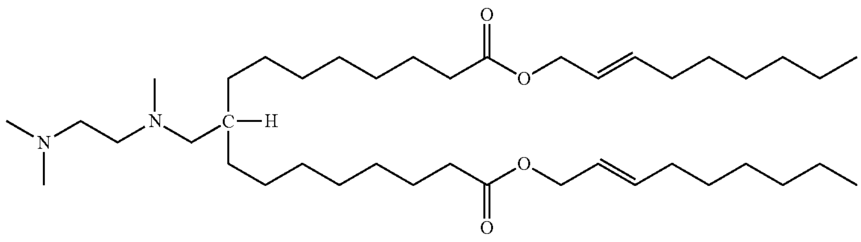

(1-02)

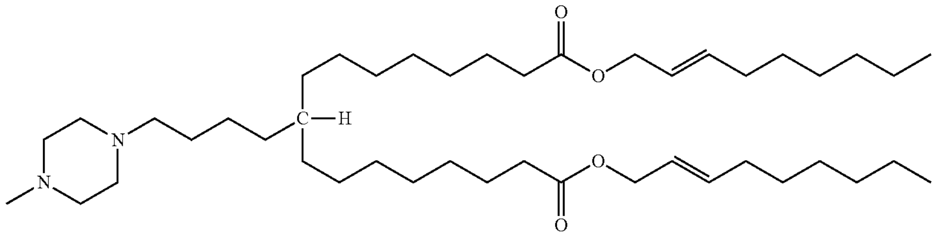

-continued

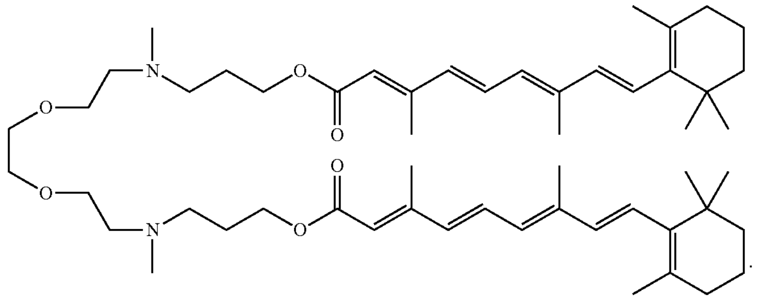

(2-01)

12. The kit according claim 10, further comprising a reagent for detecting expression of the reporter gene.

13. The kit according claim 10, further comprising estrogen.

14. A method for detecting an estrogen-sensitive cell in a test cell by using a nucleic acid construct, the nucleic acid construct including:

an enhancer sequence including at least an ERE sequence and at least a XRE sequence;

a promoter sequence ligated to downstream of the enhancer sequence; and a reporter gene ligated to downstream of the promoter sequence, the detection method comprising:

introducing the nucleic acid construct into the test cell;

adding estrogen to the test cell;

culturing the test cell;

detecting an activity of a reporter protein expressed from the reporter gene; and determining the estrogen-sensitive cell from a result of the detection.

15. The method according to claim 14, wherein the introducing is performed by bringing a lipid particle encapsulating the nucleic acid into contact with the test cell.

16. The method according to claim 14, wherein the cell having high activity of the reporter gene is determined to be an estrogen-sensitive cell.

17. The method according to claim 14, wherein the culturing and the detecting are performed on a CMOS image sensor.

18. The method according to claim 14, further comprising:

calculating, from the result of the detecting, an abundance ratio of the estrogen-sensitive cell by the following equation (I), abundance ratio=number of estrogen-sensitive cells/number of test cells  Equation (I); and determining an intensity of estrogen sensitivity of the test cell from the abundance ratio.

19. The method according to claim 18, wherein the determinating the intensity of estrogen sensitivity of the test cell is performed based on a previously prepared threshold value of an abundance ratio of the estrogen-sensitive cell.

20. The method according to claim 18, further comprising:

calculating a corrected value of the obtained abundance ratio by the following equation (II), corrected value of abundance ratio=the abundance ratio with the estrogen added/a abundance ratio by the detection method without the estrogen added  Equation (II); and determining an intensity of estrogen sensitivity of the test cell from the corrected value.

21. A method for predicting efficacy of hormone treatment for cancer in a subject, by using a nucleic acid construct, the nucleic acid construct including:

an enhancer sequence including at least an ERE sequence and at least a XRE sequence;

a promoter sequence ligated to downstream of the enhancer sequence; and a reporter gene ligated to downstream of the promoter sequence, the method comprising:

introducing the nucleic acid construct into a test cell obtained from the subject;

adding estrogen to the test cell;

culturing the test cell;

detecting activity of a reporter protein expressed from the reporter gene; and predicting efficacy of hormone treatment for cancer in the subject from a result of the detection.

22. The method according to claim 21, wherein the predicting determines that hormone therapy is effective for cancer in the subject when the activity of the reporter gene is high.

23. The method according to claim 22, wherein the test cell is a breast cancer cell or an endometrial cancer cell.

* * * * *